(12) United States Patent
Merali et al.

(10) Patent No.: US 9,933,435 B2
(45) Date of Patent: Apr. 3, 2018

(54) DIAGNOSIS AND TREATMENT OF CHRONIC OBSTRUCTIVE PULMONARY DISEASE (COPD) BASED ON ELEVATED LEVELS OF EXTRACELLULAR H3 PROTEIN

(71) Applicant: TEMPLE UNIVERSITY—OF THE COMMONWEALTH SYSTEM OF HIGHER EDUCATION, Philadelphia, PA (US)

(72) Inventors: Salim Merali, Bryn Mawr, PA (US); Camilo Moncada, Philadelphia, PA (US); Steven G. Kelsen, Rydal, PA (US); Carlos A. Barrero, Philadelphia, PA (US); Oscar Mauricio Perez Leal, Barranquilla (CO)

(73) Assignee: TEMPLE UNIVERSITY-OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

(21) Appl. No.: 15/044,649

(22) Filed: Feb. 16, 2016

(65) Prior Publication Data
US 2016/0187353 A1  Jun. 30, 2016

Related U.S. Application Data

(62) Division of application No. 14/117,157, filed as application No. PCT/US2012/037501 on May 11, 2012, now Pat. No. 9,291,626.

(60) Provisional application No. 61/485,379, filed on May 12, 2011.

(51) Int. Cl.
 G01N 33/68 (2006.01)
 G01N 33/577 (2006.01)
 H01J 49/00 (2006.01)

(52) U.S. Cl.
 CPC ....... *G01N 33/6875* (2013.01); *G01N 33/577* (2013.01); *H01J 49/0027* (2013.01); *G01N 2440/12* (2013.01); *G01N 2800/122* (2013.01); *G01N 2800/56* (2013.01)

(58) Field of Classification Search
 CPC ............ G01N 33/6875; G01N 33/577; G01N 2800/56; G01N 2800/122; G01N 2440/12; H01J 49/0027
 See application file for complete search history.

(56) References Cited

U.S. PATENT DOCUMENTS

2005/0089517 A1  4/2005  Shames
2008/0138913 A1  6/2008  Jeon et al.
2010/0129926 A1  5/2010  Spiteri
2010/0151468 A1  6/2010  Esteller et al.
2011/0097752 A1  4/2011  Ankersmit

FOREIGN PATENT DOCUMENTS

WO  WO-2010000820 A2  1/2010

OTHER PUBLICATIONS

Barrero et al., "Extracellular Histones in the COPD Lung are Cytotoxic", Scientific Abstract 20899:Category 09.10-COPD Pathogenesis (CP) May 16, 2011.
Szulakowski et al. "The Effect of Smoking on the Transcriptional Regulation of Lung Inflammation in Patients with Chronic Obstructive Pulmonary Disease", Am J Respir Crit Care Med, 174: 41-50, 2006.
Garcia et al. "Modifications of Human Histone H3 Variants during Mitosis", Biochemistry, 44: 13202-13213, 2005.
Hake et al. "Expression Patterns and Post-translational Modifications Associated with Mammalian Histone H3 Variants", The Journal of Biological Chemistry, 281:1 559-568, 2006.
Barski et al. "High-Resolution Profiling of Histone Methylations in the Human Genome", Cell, 129: 823-837, 2007.
Boyne et al. "Tandem Mass Spectrometry with Ultrahigh Mass Accuracy Clarifies Peptide Identification by Database Retrieval", J Proteome Res, 8:1 374-379, 2009.
Tsao et al. "Notch signaling controls the balance of ciliated and secretory cell fates in developing airways", Development and Disease, 136:13 2297-2307, 2009.
Dominguez et al. "Chromatin and the cell cycle meet in Madrid" Development, 135:21 3475-3480, 2008.
Torres-Padilla et al. "Dynamic distribution of the replacement histone variant H3.3 in the mouse oocyte and preimplantation embryos", Int. J. Dev. Biol., 50:5 455-461, 2006.
Anonymous: "UNIPROT:P84243", Jan. 23, 2007, XP055151946, Retrieved from the Internet: URL:http://ibis/exam/dbfetch.jsp?id=UNIPROT%3AP84243.
Kazuto Sugimura et al: "Cell cycle-dependent accumulation of histone H3.3 and euchromatic histone modifications in pericentromeric heterochromatin in response to a decrease in DNA methylation levels", Experimental Cell Research, vol. 316, No. 17, Oct. 1, 2010, pp. 2731-2746.
Alejandra Loyola et al: "PTMs on H3 Variants before Chromatin Assembly Potentiate Their Final Epigenetic State", Molecular Cell, vol. 24, No. 2, Oct. 1, 2006, pp. 309-316.
Stefan Hacker et al: "Increased soluble serum markers caspase-cleaved cytokeratin-18, histones, and ST2 indicate apoptotic turnover and chronic immune response in COPD", Journal of Clinical Laboratory Analysis, vol. 23, No. 6, Jan. 1, 2009, pp. 372-379.

(Continued)

Primary Examiner — Robert S Landsman
(74) Attorney, Agent, or Firm — Drinker Biddle & Reath LLP

(57) ABSTRACT

Provided is a method for diagnosing and/or staging COPD based on detection of one or more histone proteins. In some embodiments, the histone protein is an H3.3 protein comprising a post-translational modification. In some embodiments, the histone protein is H2B, H3, H3.3 or H4. Kits for practicing the methods of diagnosis and/or staging are provided as well. Further provided is a method for treating COPD.

18 Claims, 10 Drawing Sheets

(56) References Cited

OTHER PUBLICATIONS

Alexandra Schulmeister et al: "Phosphorylation of the histone H3.3 variant in mitosis and meiosis of the urochordate Oikopleura dioica", Chromosome Research, Kluwer Academic Publishers, DO, vol. 15, No. 2, Feb. 15, 2007, pp. 189-201.
Peter J. Barnes, et al: Reduced Histone Deacetylase in COPD**, Chest, vol. 129, No. 1, Jan. 1, 2006, p. 151.
Kazuhiro Ito et al: "Decreased Histone Deacetylase Activity in Chronic Obstructive Pulmonary Disease Background", N. Engl. J. Med, Jan. 1, 2005, pp. 1967-1976. Retrieved from the Internet: URL:http://www.nejm.org/doi/pdf/10.1056/ NEJMoa041892.
Hye Ryung Jung et al: "Quantitative mass spectrometry of histones H3.2 and H3.3 in Suz12-deficient mouse embroyonic stem cells reveals distinct, dynamic post-translational modifications at Lys-27 and Lys-36", Molecular & Cellular proteomics: MCP, May 1, 2010, pp. 838-850. Retrieved from the Internet: URL:http://www.ncbi.nlm,nih.gov/pubmed/20150217.
Selvi et al., Reversible acetylation of chromatin, Biotechnol. J. 4:375-390 (2009).
Barrero et al., Proteomics analysis of lung nuclear proteins in COPD, Am. J. Resp. Crit. Care Med 181:A3830 (2010).
Rahman et al., Oxidative stress and redox regulation of lung inflammation in COPD., Eur. Respir. J. 28:219-242 (2006).
Szulakowski et al., The effect of smoking on the transcriptional regulation of lung inflammation in patients with COPD, Am J Respir Crit Care Med 174:41-50, (2006).
Ito, Impact of post-translational modifications of proteins on the inflammatory process, Biochemical society transactions, vol. 35:2 (2007).
Adenuga et al., Oxidative stress, histone deacetylase and corticosteroid resistance in severe asthma and COPD, Current respiratory medicine reviews 3(1):57-68 (2007).
Adcock et al., Epigenetic regulation of airway inflammation, Current opinion in immunology, 19(6):694-700 (2007).
Nuñez et al., A. Anti-tissue antibodies are related to lung function in chronic obstructive pulmonary disease. AJRCCM Articles in Press. Published on Nov. 19, 2010 as doi:10.1164/rccm.201001-0029OC.
Nicodeme et al., Suppression of inflammation by a synthetic histone mimic. Nature 000: 1-5 (2010) doi:10.1038/nature09589.
Hake et al., Histone H3 variants and their potential role in indexing mammalian genomes: The "H3 barcode hypothesis" PNAS 103(17):6428-6435.
Barnes, Reduced histone deacetylase in COPD: Clinical implications. Chest (2006) 129:151-155.
Yokohori et al., Increased levels of cell death and proliferation in alveolar wall cells in patients with pulmonary emphysema. Chest 125, 626-632 (2004).
Yao et al., Redox regulation of lung inflammation: role of NADPH oxidase and NF-kB signaling. Biochemical society transactions (2007) 35:1151-1155.
Agusti, COPD, a multicomponent disease: implications for management. Respir Med 99, 670-682 (2005).
Barnes, Histone deacetylase-2 and airway disease. Ther Adv Respir Dis 3, 235-243 (2009a).
Barnes, Role of HDAC2 in the pathophysiology of COPD. Annual review of physiology 71, 451-464 (2009b).
Barnes, Targeting the epigenome in the treatment of asthma and chronic obstructive pulmonary disease. Proc Am Thorac Soc 6, 693-696 (2009c).
Bhavsar et al, The role of histone deacetylases in asthma and allergic diseases. J Allergy Clin Immunol 121, 580-584 (2008).
Demedts et al., Role of apoptosis in the pathogenesis of COPD and pulmonary emphysema. Respir Res 7, 53 (2006).
Gabler et al., Accumulation of histones in cell lysates precedes expression of apoptosis-related phagocytosis signals in human lymphoblasts. Ann N Y Acad Sci 1010, 221-224 (2003).
Godtfredsen et al., COPD-related morbidity and mortality after smoking cessation: status of the evidence. Eur Respir J 32, 844-853 (2008).
Gonzalez et al., The expression of adhesion molecules in cigarette smoke-induced airways obstruction. Eur Respir J 9, 1995-2001 (1996).
Yu et al., Histone acetylation, chromatin remodelling and nucleotide excision repair: hint from the study on MFA2 in *Saccharomyces cerevisiae*. Cell Cycle 4, 1043-1045 (2005).
Kasahara et al., Inhibition of VEGF receptors causes lung cell apoptosis and emphysema. J Clin Invest 106, 1311-1319 (2000).
Xu et al., Extracellular histones are major mediators of death in sepsis. Nat Med 15, 1318-1321 (2009).
Wood et al., Post-translational modifications of the linker histone variants and their association with cell mechanisms. FEBS J 276, 3685-3697 (2009).
Lee et al., Chronic inflammation, chronic obstructive pulmonary disease, and lung cancer. Curr Opin Pulm Med (2009).
Maclay et al., Update in chronic obstructive pulmonary disease 2008. American journal of respiratory and critical care medicine 179, 533-541 (2009).
Macnee, Pathogenesis of chronic obstructive pulmonary disease. Proc Am Thorac Soc vol. 2 pp. 258-266 (2005).
Makris et al., Increased apoptosis of neutrophils in induced sputum of COPD patients. Respir Med 103, 1130-1135 (2009).
Mannino et al., Chronic obstructive pulmonary disease and hospitalizations for pneumonia in a US cohort. Respir Med 103, 224-229 (2009).
Papayannopoulos et al., NETs: a new strategy for using old weapons. Trends Immunol 30, 513-521 (2009).
Pemberton et al., Proteomic identification of interactions between histones and plasma proteins: implications for cytoprotection. Proteomics 10, 1484-1493 (2010).
Postma et al., Remodeling in asthma and chronic obstructive pulmonary disease. Proc Am Thorac Soc 3, 434-439 (2006).
Rajendrasozhan et al., Current perspectives on role of chromatin modifications and deacetylases in lung inflammation in COPD. COPD 6, 291-297 (2009).
Richens et al., Cigarette smoke impairs clearance of apoptotic cells through oxidant-dependent activation of RhoA. American journal of respiratory and critical care medicine 179, 1011-1021 (2009).
Salazar et al., Fibrotic response of tissue remodeling in COPD. Lung 189, 101-109 (2011).
Wiesner et al., Antimicrobial peptides: the ancient arm of the human immune system. Virulence 1, 440-464 (2010).
Voigt et al., Histone tails: ideal motifs for probing epigenetics through chemical biology approaches. Chembiochem 12, 236-252 (2011).
Weake et al., Inducible gene expression: diverse regulatory mechanisms. Nat Rev Genet 11, 426-437 (2010).
Westergren-Thorsson et al., Pathological airway remodelling in inflammation. Clin Respir J 4 Suppl 1, 1-8 (2010).
Macnee, Pulmonary and Systemic Oxidant/Antioxidant Imbalance in Chronic Obstructive Pulmonary Disease. Proc Am Thorac Soc vol. 2 pp. 50-60 (2005).
Nicodeme et al., "Suppression of inflammation by a synthetic histone mimic," Nature 468 (7327):1119-23 (2010) doi:10.1038/nature09589.

SEQUENCE LISTING

```
<160> NUMBER OF SEQ ID NOS: 32

<210> SEQ ID NO 1
<211> LENGTH: 136
<212> TYPE: PRT
<213> ORGANISM: Homo sapiens

<400> SEQUENCE: 1

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45
```

```
Leu Arg Glu Ile Arg Arg Tyr Gln Lys Ser Thr Glu Leu Leu Ile Arg
 50                  55                  60
Lys Leu Pro Phe Gln Arg Leu Val Arg Glu Ile Ala Gln Asp Phe Lys
 65                  70                  75                  80
Thr Asp Leu Arg Phe Gln Ser Ala Ala Ile Gly Ala Leu Gln Glu Ala
                 85                  90                  95
Ser Glu Ala Tyr Leu Val Gly Leu Phe Glu Asp Thr Asn Leu Cys Ala
                100                 105                 110
Ile His Ala Lys Arg Val Thr Ile Met Pro Lys Asp Ile Gln Leu Ala
                115                 120                 125
Arg Arg Ile Arg Gly Glu Arg Ala
    130                 135

<210> SEQ ID NO 2
<211> LENGTH: 130
<212> TYPE: PRT
<213> ORGANISM: Homo sapiens

<400> SEQUENCE: 2

Met Ser Gly Arg Gly Lys Gln Gly Gly Lys Ala Arg Ala Lys Ala Lys
  1               5                  10                  15
Thr Arg Ser Ser Arg Ala Gly Leu Gln Phe Pro Val Gly Arg Val His
                 20                  25                  30
Arg Leu Leu Arg Lys Gly Asn Tyr Ala Glu Arg Val Gly Ala Gly Ala
                 35                  40                  45
Pro Val Tyr Leu Ala Ala Val Leu Glu Tyr Leu Thr Ala Glu Ile Leu
 50                  55                  60
Glu Leu Ala Gly Asn Ala Ala Arg Asp Asn Lys Lys Thr Arg Ile Ile
 65                  70                  75                  80
Pro Arg His Leu Gln Leu Ala Ile Arg Asn Asp Glu Glu Leu Asn Lys
                 85                  90                  95
Leu Leu Gly Lys Val Thr Ile Ala Gln Gly Gly Val Leu Pro Asn Ile
                100                 105                 110
Gln Ala Val Leu Leu Pro Lys Lys Thr Glu Ser His His Lys Ala Lys
                115                 120                 125
Gly Lys
    130

<210> SEQ ID NO 3
<211> LENGTH: 127
<212> TYPE: PRT
<213> ORGANISM: Homo sapiens

<400> SEQUENCE: 3

Met Pro Glu Val Ser Ser Lys Gly Ala Thr Ile Ser Lys Lys Gly Phe
  1               5                  10                  15
Lys Lys Ala Val Val Lys Thr Gln Lys Lys Glu Gly Lys Lys Arg Lys
                 20                  25                  30
Arg Thr Arg Lys Glu Ser Tyr Ser Ile Tyr Ile Tyr Lys Val Leu Lys
                 35                  40                  45
Gln Val His Pro Asp Thr Gly Ile Ser Ser Lys Ala Met Ser Ile Met
 50                  55                  60
Asn Ser Phe Val Thr Asp Ile Phe Glu Arg Ile Ala Ser Glu Ala Ser
 65                  70                  75                  80
Arg Leu Ala His Tyr Ser Lys Arg Ser Thr Ile Ser Ser Arg Glu Ile
                 85                  90                  95
```

```
Gln Thr Ala Val Arg Leu Leu Leu Pro Gly Glu Leu Ala Lys His Ala
            100                 105                 110

Val Ser Glu Gly Thr Lys Ala Val Thr Lys Tyr Thr Ser Ser Lys
        115                 120                 125

<210> SEQ ID NO 4
<211> LENGTH: 126
<212> TYPE: PRT
<213> ORGANISM: Homo sapiens

<400> SEQUENCE: 4

Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Arg Lys Arg Lys Arg
            20                  25                  30

Ser Arg Lys Glu Ser Tyr Ser Val Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Pro His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ala Lys
        115                 120                 125

<210> SEQ ID NO 5
<211> LENGTH: 136
<212> TYPE: PRT
<213> ORGANISM: Homo sapiens

<400> SEQUENCE: 5

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 6
<211> LENGTH: 136
<212> TYPE: PRT
<213> ORGANISM: Homo sapiens
```

<400> SEQUENCE: 6

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 7
<211> LENGTH: 103
<212> TYPE: PRT
<213> ORGANISM: Homo sapiens

<400> SEQUENCE: 7

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 8
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: post-translational modification: acetylation

<400> SEQUENCE: 8

Arg Lys Gln Leu Ala Thr Lys Ala Ala Arg Lys
1               5                   10

<210> SEQ ID NO 9
<211> LENGTH: 34
<212> TYPE: PRT
<213> ORGANISM: Homo sapiens
<220> FEATURE:

```
<221> NAME/KEY: MOD_RES
<222> LOCATION: (28)..(28)
<223> OTHER INFORMATION: post-translational modification:
      carbamidomethylation
<220> FEATURE:
<221> NAME/KEY: MOD_RES
<222> LOCATION: (33)..(33)
<223> OTHER INFORMATION: post-translational modification: methylation

<400> SEQUENCE: 9

Arg Phe Gln Ser Ala Ala Ile Gly Ala Leu Gln Glu Ala Ser Glu Ala
1               5                   10                  15

Tyr Leu Val Gly Leu Phe Glu Asp Thr Asn Leu Cys Ala Ile His Ala
            20                  25                  30

Lys Arg

<210> SEQ ID NO 10
<211> LENGTH: 11
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: post-translational modification: acetylation
<220> FEATURE:
<221> NAME/KEY: MOD_RES
<222> LOCATION: (7)..(7)
<223> OTHER INFORMATION: post-translational modification: acetylation

<400> SEQUENCE: 10

Arg Lys Gln Leu Ala Thr Lys Ala Ala Arg Lys
1               5                   10

<210> SEQ ID NO 11
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: post-translational modification: methylation

<400> SEQUENCE: 11

Arg Glu Ile Ala Gln Asp Phe Lys Thr Asp Leu Arg Phe
1               5                   10

<210> SEQ ID NO 12
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: post-translational modification: deamidation
<220> FEATURE:
<221> NAME/KEY: MOD_RES
<222> LOCATION: (6)..(6)
<223> OTHER INFORMATION: post-translational modification: methylation
<220> FEATURE:
<221> NAME/KEY: MOD_RES
<222> LOCATION: (8)..(8)
<223> OTHER INFORMATION: post-translational modification: acetylation

<400> SEQUENCE: 12

Arg Glu Ile Ala Gln Asp Phe Lys Thr Asp Leu Arg Phe
1               5                   10

<210> SEQ ID NO 13
<211> LENGTH: 13
```

```
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: post-translational modification:
      ubiquitinylation (trypsin digest results in diglycine adduct)

<400> SEQUENCE: 13

Arg Glu Ile Ala Gln Asp Phe Lys Thr Asp Leu Arg Phe
1               5                   10

<210> SEQ ID NO 14
<211> LENGTH: 34
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: post-translational modification: deamidation
<220> FEATURE:
<221> NAME/KEY: MOD_RES
<222> LOCATION: (11)..(11)
<223> OTHER INFORMATION: post-translational modification: deamidation
<220> FEATURE:
<221> NAME/KEY: MOD_RES
<222> LOCATION: (23)..(23)
<223> OTHER INFORMATION: post-translational modification: methylation
<220> FEATURE:
<221> NAME/KEY: MOD_RES
<222> LOCATION: (26)..(26)
<223> OTHER INFORMATION: post-translational modification: deamidation
<220> FEATURE:
<221> NAME/KEY: MOD_RES
<222> LOCATION: (33)..(33)
<223> OTHER INFORMATION: post-translational modification: acetylation

<400> SEQUENCE: 14

Arg Phe Gln Ser Ala Ala Ile Gly Ala Leu Gln Glu Ala Ser Glu Ala
1               5                   10                  15

Tyr Leu Val Gly Leu Phe Glu Asp Thr Asn Leu Cys Ala Ile His Ala
            20                  25                  30

Lys Arg

<210> SEQ ID NO 15
<211> LENGTH: 16
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: post-translational modification: dimethylation
<220> FEATURE:
<221> NAME/KEY: MOD_RES
<222> LOCATION: (12)..(12)
<223> OTHER INFORMATION: post-translational modification: dimethylation

<400> SEQUENCE: 15

Arg Lys Ser Ala Pro Ser Thr Gly Gly Val Lys Lys Pro His Arg Tyr
1               5                   10                  15

<210> SEQ ID NO 16
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: post-translational modification: methylation

<400> SEQUENCE: 16
```

Arg Glu Ile Ala Gln Asp Phe Lys Thr Asp Leu Arg Phe
1               5                  10

<210> SEQ ID NO 17
<211> LENGTH: 34
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: post-translational modification: methylation
<220> FEATURE:
<221> NAME/KEY: MOD_RES
<222> LOCATION: (24)..(24)
<223> OTHER INFORMATION: post-translational modification: methylation
<220> FEATURE:
<221> NAME/KEY: MOD_RES
<222> LOCATION: (28)..(28)
<223> OTHER INFORMATION: post-translational modification: nitrosylation
<220> FEATURE:
<221> NAME/KEY: MOD_RES
<222> LOCATION: (33)..(33)
<223> OTHER INFORMATION: post-translational modification: methylation

<400> SEQUENCE: 17

Arg Phe Gln Ser Ala Ala Ile Gly Ala Leu Gln Glu Ala Ser Glu Ala
1               5                   10                  15

Tyr Leu Val Gly Leu Phe Glu Asp Thr Asn Leu Cys Ala Ile His Ala
            20                  25                  30

Lys Arg

<210> SEQ ID NO 18
<211> LENGTH: 11
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: post-translational modification: acetylation
<220> FEATURE:
<221> NAME/KEY: MOD_RES
<222> LOCATION: (7)..(7)
<223> OTHER INFORMATION: post-translational modification: acetylation

<400> SEQUENCE: 18

Arg Lys Ser Thr Gly Gly Lys Ala Pro Arg Lys
1               5                   10

<210> SEQ ID NO 19
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: post-translational modification: acetylation

<400> SEQUENCE: 19

Arg Lys Gln Leu Ala Thr Lys Ala Ala Arg Lys
1               5                   10

<210> SEQ ID NO 20
<211> LENGTH: 11
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: post-translational modification: acetylation

```
<220> FEATURE:
<221> NAME/KEY: MOD_RES
<222> LOCATION: (7)..(7)
<223> OTHER INFORMATION: post-translational modification: acetylation

<400> SEQUENCE: 20

Arg Lys Gln Leu Ala Thr Lys Ala Ala Arg Lys
1               5                   10

<210> SEQ ID NO 21
<211> LENGTH: 34
<212> TYPE: PRT
<213> ORGANISM: Homo sapiens
<220> FEATURE:
<221> NAME/KEY: MOD_RES
<222> LOCATION: (33)..(33)
<223> OTHER INFORMATION: post-translation modifications: lysine
      acetylation and methylation (C-term)

<400> SEQUENCE: 21

Arg Phe Gln Ser Ala Ala Ile Gly Ala Leu Gln Glu Ala Ser Glu Ala
1               5                   10                  15

Tyr Leu Val Gly Leu Phe Glu Asp Thr Asn Leu Cys Ala Ile His Ala
            20                  25                  30

Lys Arg

<210> SEQ ID NO 22
<211> LENGTH: 34
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: post-translational modification: methylation
<220> FEATURE:
<221> NAME/KEY: MOD_RES
<222> LOCATION: (33)..(33)
<223> OTHER INFORMATION: post-translation modifications: lysine
      acetylation and methylation (C-term)

<400> SEQUENCE: 22

Arg Phe Gln Ser Ala Ala Ile Gly Ala Leu Gln Glu Ala Ser Glu Ala
1               5                   10                  15

Tyr Leu Val Gly Leu Phe Glu Asp Thr Asn Leu Cys Ala Ile His Ala
            20                  25                  30

Lys Arg

<210> SEQ ID NO 23
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: post-translational modification: oxidation

<400> SEQUENCE: 23

Lys Arg Val Thr Ile Met Pro Lys Asp
1               5

<210> SEQ ID NO 24
<211> LENGTH: 12
<212> TYPE: PRT
<213> ORGANISM: Homo sapiens
<220> FEATURE:
<221> NAME/KEY: MOD_RES
<222> LOCATION: (2)..(2)
```

```
<223> OTHER INFORMATION: post-translational modification: dimethylation

<400> SEQUENCE: 24

Arg Lys Ser Ala Pro Ser Thr Gly Gly Val Lys Lys
1               5                   10

<210> SEQ ID NO 25
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: post-translational modification: methylation

<400> SEQUENCE: 25

Arg Glu Ile Ala Gln Asp Phe Lys Thr Asp Leu Arg Phe
1               5                   10

<210> SEQ ID NO 26
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: post-translational modification: dimethylation

<400> SEQUENCE: 26

Arg Tyr Arg Pro Gly Thr Val Ala Leu Arg Glu
1               5                   10

<210> SEQ ID NO 27
<211> LENGTH: 11
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: post-translational modification: acetylation
<220> FEATURE:
<221> NAME/KEY: MOD_RES
<222> LOCATION: (7)..(7)
<223> OTHER INFORMATION: post-translational modification: acetylation

<400> SEQUENCE: 27

Arg Lys Gln Leu Ala Thr Lys Ala Ala Arg Lys
1               5                   10

<210> SEQ ID NO 28
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: post-translational modification:
      ubiquitinylation (trypsin digest results in diglycine adduct)

<400> SEQUENCE: 28

Arg Glu Ile Ala Gln Asp Phe Lys Thr Asp Leu Arg Phe
1               5                   10

<210> SEQ ID NO 29
<211> LENGTH: 34
<212> TYPE: PRT
<213> ORGANISM: Homo sapiens
<220> FEATURE:
<221> NAME/KEY: MOD_RES
```

```
<222> LOCATION: (11)..(11)
<223> OTHER INFORMATION: post-translational modification: deamidation
<220> FEATURE:
<221> NAME/KEY: MOD_RES
<222> LOCATION: (23)..(23)
<223> OTHER INFORMATION: post-translational modification: methylation
<220> FEATURE:
<221> NAME/KEY: MOD_RES
<222> LOCATION: (26)..(26)
<223> OTHER INFORMATION: post-translational modification: deamidation
<220> FEATURE:
<221> NAME/KEY: MOD_RES
<222> LOCATION: (33)..(33)
<223> OTHER INFORMATION: post-translational modification: acetylation

<400> SEQUENCE: 29

Arg Phe Gln Ser Ala Ala Ile Gly Ala Leu Gln Glu Ala Ser Glu Ala
1               5                   10                  15

Tyr Leu Val Gly Leu Phe Glu Asp Thr Asn Leu Cys Ala Ile His Ala
            20                  25                  30

Lys Arg

<210> SEQ ID NO 30
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: post-translational modification: methylation

<400> SEQUENCE: 30

Arg Glu Ile Ala Gln Asp Phe Lys Thr Asp Leu Arg Phe
1               5                   10

<210> SEQ ID NO 31
<211> LENGTH: 14
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: post-translational modification:
      trimethylation
<220> FEATURE:
<221> NAME/KEY: MOD_RES
<222> LOCATION: (10)..(10)
<223> OTHER INFORMATION: post-translational modification: methylation

<400> SEQUENCE: 31

Asp Arg Glu Ile Ala Gln Asp Phe Lys Thr Asp Leu Arg Phe
1               5                   10

<210> SEQ ID NO 32
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: post-translational modification: acetylation

<400> SEQUENCE: 32

Lys Gln Leu Ala Thr Lys Ala Ala Arg
1               5
```

DIAGNOSIS AND TREATMENT OF CHRONIC OBSTRUCTIVE PULMONARY DISEASE (COPD) BASED ON ELEVATED LEVELS OF EXTRACELLULAR H3 PROTEIN

CROSS-REFERENCE TO RELATED APPLICATION

This is a divisional of application Ser. No. 14/117,157 filed Nov. 27, 2013, now U.S. Pat. No. 9,291,626, which is the U.S. national stage of International Application PCT/US2012/037501, filed May 11, 2012, which claims the benefit of the filing date of U.S. Provisional Patent Application No. 61/485,379, filed May 12, 2011. The entire disclosures of the aforesaid applications are incorporated herein by reference.

REFERENCE TO GOVERNMENT GRANT

The invention described herein was supported in part by the National Institutes of Health, under grant no. 5RC2HL101713-02. The government has certain rights in this invention.

SEQUENCE LISTING

The instant application contains a Sequence Listing which has been submitted in ASCII format via EFS-Web and is hereby incorporated by reference in its entirety. Said ASCII copy, created on Feb. 16, 2016 is named 35926_431_01.txt and is 18,626 bytes in size.

FIELD OF THE INVENTION

The invention relates to a method for the diagnosis and treatment of chronic obstructive pulmonary disease (COPD).

BACKGROUND OF THE INVENTION

Chronic obstructive pulmonary disease (COPD), a disease characterized by inflammation, cell death and extensive lung tissue remodeling, is an increasingly important public health concern in the United States and worldwide (Lee et al. 2009; Maclay et al. 2009). COPD is the fourth leading cause of death worldwide and the World Health Organization predicts that by the year 2030 COPD will become the third leading cause of death (Godtfredsen et al. 2008). It is estimated that 170,000 Americans die of COPD annually and direct and indirect expenditures on COPD exceed 48 billion dollars (Mannino et al. 2009). While research efforts have led to decreases in the prevalence of most diseases, COPD is on the rise in first world countries (Lee et al. 2009; Maclay et al. 2009).

Although the molecular mechanisms underlying development of COPD remain incompletely understood, heightened expression of pro-inflammatory molecules, lung cell death and tissue remodeling are believed to play critical roles. (Postma and Timens, 2006; Salazar and Herrera, 2011; Westergren-Thorsson et al., 2010) The intensity of inflammatory responses and alterations in cell behavior reflect both the activation state of signaling proteins upstream of genes of interest and signal-induced assembly of nuclear chromatin complexes that support the formation of mRNA. Specifically, in COPD, alterations in gene expression result both from activation of key transcription factors and from epigenetic changes which affect chromatin remodeling (e.g., altered histone acetylation). (Macnee, 2007; Rajendrasozhan et al., 2009)

Nuclear chromatin which includes the several histones is the cell scaffolding which promotes the interaction between DNA and the transcription factors which affect gene expression (Lamond and Earnshaw 1998). Post-translational modification of histones affects gene regulation (Taverna et al., 2007; Voigt and Reinberg, 2011; Wood et al., 2009) In fact, changes in histone acetylation induced by reductions in histone deacetylase (HDAC) expression contribute to the heightened inflammatory state present in the lung in COPD (Barnes, 2009a, b; Bhavsar et al., 2008). Of interest, however, histones also exert diverse functions when present extracellularly (Papayannopoulos and Zychlinsky, 2009; Wiesner and Vilcinskas, 2010) For example, histones are potent anti-microbials, more potent than conventional antibiotics (Kawasaki and Iwamuro, 2008; Papayannopoulos and Zychlinsky, 2009; Wiesner and Vilcinskas 2010) Moreover, while histones are not generally believed to be noxious, they induce lung inflammation and damage when present in the circulation and are cytotoxic to human lung cells when present in the extracellular space. (Xu et al., 2009)

Chromatin remodeling and epigenetic changes determine gene transcription by affecting transcription factor and RNA polymerase binding to DNA (Weake and Workman, 2010; Yu and Waters, 2005). In particular, post-translational modification of amino acids in core histones including lysine hyper acetylation induces inflammatory gene expression in COPD (Barnes, 2009a, c; Bhavsar et al., 2008). However, the nature of other post-translational modifications in COPD and the discrete amino acids involved remain poorly understood.

What is needed are methods of diagnosing and staging COPD, as well as methods of treating COPD.

SUMMARY OF THE INVENTION

Provided is a method for diagnosing chronic obstructive pulmonary disease (COPD) comprising measuring the level of extracellular H2B, H3, H3.3 or H4 protein in a test sample of a patient and comparing the level of extracellular H2B, H3, H3.3 or H4 protein to the extracellular level of H2B, H3, H3.3 or H4 protein respectively in a control sample, wherein an elevated level of extracellular H2B, H3, H3.3 or H4 protein in the test sample of the patient as compared to the level of extracellular H2B, H3, H3.3 or H4 protein respectively in the control sample indicates that the patient suffers from COPD. In some embodiments, the level of extracellular H2B, H3, H3.3 or H4 is 1.2, 1.3, 1.4, 1.5, 2, 2.5, 3, 3.5, 4, 5, 6, 6.5, 7 or 8 times that of the control. In some preferred embodiments, the control sample is from a healthy person without COPD. In further preferred embodiments, the control is from an ex-smoker without COPD. In yet further preferred embodiments, the control sample is from a GOLD 0 patient (at risk of developing COPD as defined below). In preferred embodiments, the test sample is from the airway of the patient. In some embodiments, the test sample comprises mucus plugs from the airway of the patient. In some embodiments, the test sample comprises cell debris that was attached to the cilia of airway epithelial cells of the patient or the control. In further embodiments, the test sample comprises bronchoalveolar fluid of the patient. In yet further embodiments, the extracellular H2B, H3, H3.3 or H4 protein is measured in a test sample comprising a biological fluid sample of the patient. In preferred embodiments, the test sample comprises plasma or serum.

Provided is a method for staging COPD comprising measuring the level of H2B, H3 or H4 protein in a test sample of a patient; and comparing the level of H2B, H3 and H4 protein to the level of H2B, H3 or H4 protein in a sample of a control healthy person without COPD, a GOLD 0 control, a GOLD I control, a GOLD II control, a GOLD III control or a GOLD IV control, determining which control has the most similar level of H2B, H3 or H4 protein to that of the patient, and assigning to the patient the stage of the control with the most similar level of H2B, H3 or H4 protein to that of the patient. In preferred embodiments, the test sample comprises nuclear lung extract.

Provided is a method for diagnosing COPD comprising detecting the level of an H3.3 protein having at least one post-translational modification from a test sample of a patient, comparing the level of the H3.3 protein with the at least one post-translational modification to the level of the H3.3 protein with the at least one post-translational modification in a control sample, wherein an elevated level of the H3.3 protein with the at least one post-translational modification in the test sample as compared to the level in the control sample indicates that the patient suffers from COPD. In preferred embodiments, the test sample comprises nuclear lung extract. In further preferred embodiments, the post-translational modification of an H3.3 protein comprises lysine acetylation or single or multiple methylation. In some embodiments, the post-translational modification of H3.3 comprise acetylation of lysine at position 10, 15, 19, 24, 80 or 116 of SEQ ID NO:1. In further embodiments, the post-translational modification of an H3.3 protein comprises dimethylation of lysine at position 28 or 38, or dimethylation of arginine at position 43, of SEQ ID NO:1. In yet further embodiments, the post-translational modification of an H3.3 protein comprises mono-methylation of lysine at position 80 or 116, mono-methylation of aspartate at position 82 or 107, or mono-methylation of glutamate at position 106 of SEQ ID NO:1. In some embodiments, the post-translational modification of an H3.3 protein comprises trimethylation of lysine at position 80 of SEQ ID NO:1. In further embodiments, the post-translational modification of an H3.3 protein comprises attachment of a GlyGly residue at position 80 of SEQ ID NO:1. In yet further embodiments, the post-translational modification of an H3.3 protein comprises nitrosylation of cysteine at position 111, or oxidation of methionine at position 121, of SEQ ID NO:1. In some embodiments, the post-translational modification of an H3.3 protein is detected by gel-based liquid chromatography-mass spectrometry (GeLC-MS), Selected Reaction Monitoring (SRM) or multiple reaction monitoring (MRM). In yet further embodiments, the post-translational modification of an H3.3 protein is detected by antibody binding. In some preferred embodiments, the control sample is from a healthy person without COPD. In further preferred embodiments, the control is from an ex-smoker without COPD. In yet further preferred embodiments, the control sample is from a GOLD 0 patient (at risk of developing COPD as defined below).

Provided is a method for diagnosing COPD comprising detecting at least one post-translational modification of an H3.3 protein from a test sample of a patient at position 10, 15, 28, 38, 43, 80, 107 or 116 of SEQ ID NO:1, wherein the presence of at least one post-translational modification indicates that the patient suffers from COPD. In preferred embodiments, the test sample comprises nuclear lung extract. In some embodiments, the post-translational modification of an H3.3 protein comprises nitrosylation of cysteine at position 111, or oxidation of methionine at position 121, of SEQ ID NO:1. In further preferred embodiments, the method for diagnosing COPD comprises detecting at least one post-translation modification of an H3.3 protein at position 10, 15, 28, 38, 43, 80, 107, or 116 of SEQ ID NO:1. In further preferred embodiments, the post-translational modification of an H3.3 protein comprises lysine acetylation or single or multiple methylation. In some embodiments, the post-translational modification of an H3.3 protein comprises acetylation of lysine at position 10, 15 or 80 of SEQ ID NO:1. In further embodiments, the post-translational modification of an H3.3 protein comprises mono-methylation of lysine at position 80 or 116 of SEQ ID NO:1. In yet further embodiments, the post-translational modification of an H3.3 protein comprises dimethylation of lysine at position 28 or dimethylation of arginine at position 43 of SEQ ID NO:1. In some embodiments, the post-translational modification of an H3.3 protein comprises trimethylation of lysine at position 80 of SEQ ID NO:1. In some embodiments, the post-translational modification of an H3.3 protein is detected by GeLC-MS. In yet further embodiments, the post-translational modification of an H3.3 protein is detected by antibody binding.

Provided is a method of treating COPD by administering to a patient suffering from COPD an agent that degrades H3.3 or targets H3.3 for degradation or inhibits the function of H3.3 or prevents the toxicity caused by H3.3. In some embodiments, the agent is DNase I, activated protein C or antibody to H3.3. In preferred embodiments, the agent is delivered to the lungs via aerosol. In another embodiment, the invention relates to an agent that degrades H3.3 or targets H3.3 for degradation or inhibits the function of H3.3 or prevents the toxicity caused by H3.3, for the treatment of COPD.

Provided is a method for diagnosing COPD comprising determining the levels of anti-H2B, anti-H3, anti-H3.3 or anti-H4 antibodies in a patient, and comparing the level of anti-H2B, anti-H3, anti-H3.3 or anti-H4 antibodies to the level of anti-H2B, anti-H3, anti-H3.3 or anti-H4 antibodies respectively in a control, wherein an elevated level of anti-H2B, anti-H3, anti-H3.3 or anti-H4 antibodies in the patient as compared to the level of anti-H2B, anti-H3, anti-H3.3 or anti-H4 antibodies in the control indicates that the patient suffers from COPD. In preferred embodiments, the anti-H3.3 antibodies specifically recognize post-translationally modified H3.3, wherein the post-translational modifications are characteristic of COPD. In some preferred embodiments, the control is an ex-smoker.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

BRIEF DESCRIPTION OF THE DRAWINGS

FIG. 1A: Western blots were performed for H2B and H3 from individual subjects used to form the pooled samples. Bands were scanned densitometrically and band density was normalized to Lamin A/C band density. FIG. 1B: H3 levels were determined in GOLD 4 and GOLD 1, 2 and 3, non-smokers (never smoked), GOLD 0 (ex-smokers), smokers and patients with other lung inflammatory diseases (sarcoidosis ("Sar"), idiopathic pulmonary fibrosis ("IPF"), and pulmonary hypertension ("PPH")) by ELISA.

FIG. 2A: Uniprot based H3.3 sequence (SEQ ID NO: 1) showing some of the post translationally modified residues identified by mass spectroscopy in COPD as compared to ex-smokers controls. See also Table 3. FIG. 2B: Identification of H3.3 peptide (aa 19-27 of SEQ ID No. 1; SEQ ID No. 32) containing K24Ac (H3.3K24Ac) using doubly charged precursor ion (m/z=441.60). FIG. 2C: Western blotting to confirm H3.3K24Ac and determine the extent of expression of this post-translational modification. Lamin A/C was used as an internal control.

FIG. 4A: ELISA quantitation of H3 in bronchoalveolar fluid of subjects with moderately severe COPD (GOLD II) and ex-smokers controls. FIG. 4B: Western blots of H3 in plasma of subjects with severe COPD (GOLD IV) and ex-smoker controls.

FIG. 5A: Determination of the histone cytotoxicity in bronchio-epithelial primary cells using a mix of purified histones and measured by flow cytometry for annexin V staining. FIG. 5B: The effect of albumin on histone cytotoxicity (top); The effect of acetylation of histones on cytotoxicity (bottom). FIG. 5C: Measurement of time dependent caspase 7 activation by Western blotting of endoplasmic reticulum (ER) enriched and cytoplasmic fractions to determine the mechanism implicated in the cytotoxicity of histones. FIG. 5D: Measurement of H3 and apoptosis hallmarker caspase 3 cleavage in lung extracts of COPD and controls.

FIG. 6A: Core histone proteins are elevated in COPD as demonstrated by SDS-PAGE of the pooled nuclear lung lysate from COPD GOLD IV (G IV) (n=5) and GOLD 0 (G0) controls (n=5). FIG. 6B: Bar-graph showing the similar distribution of the total proteins identified by mass spectroscopy in COPD GIV and Control G0.

DEFINITIONS

Figure 1A:
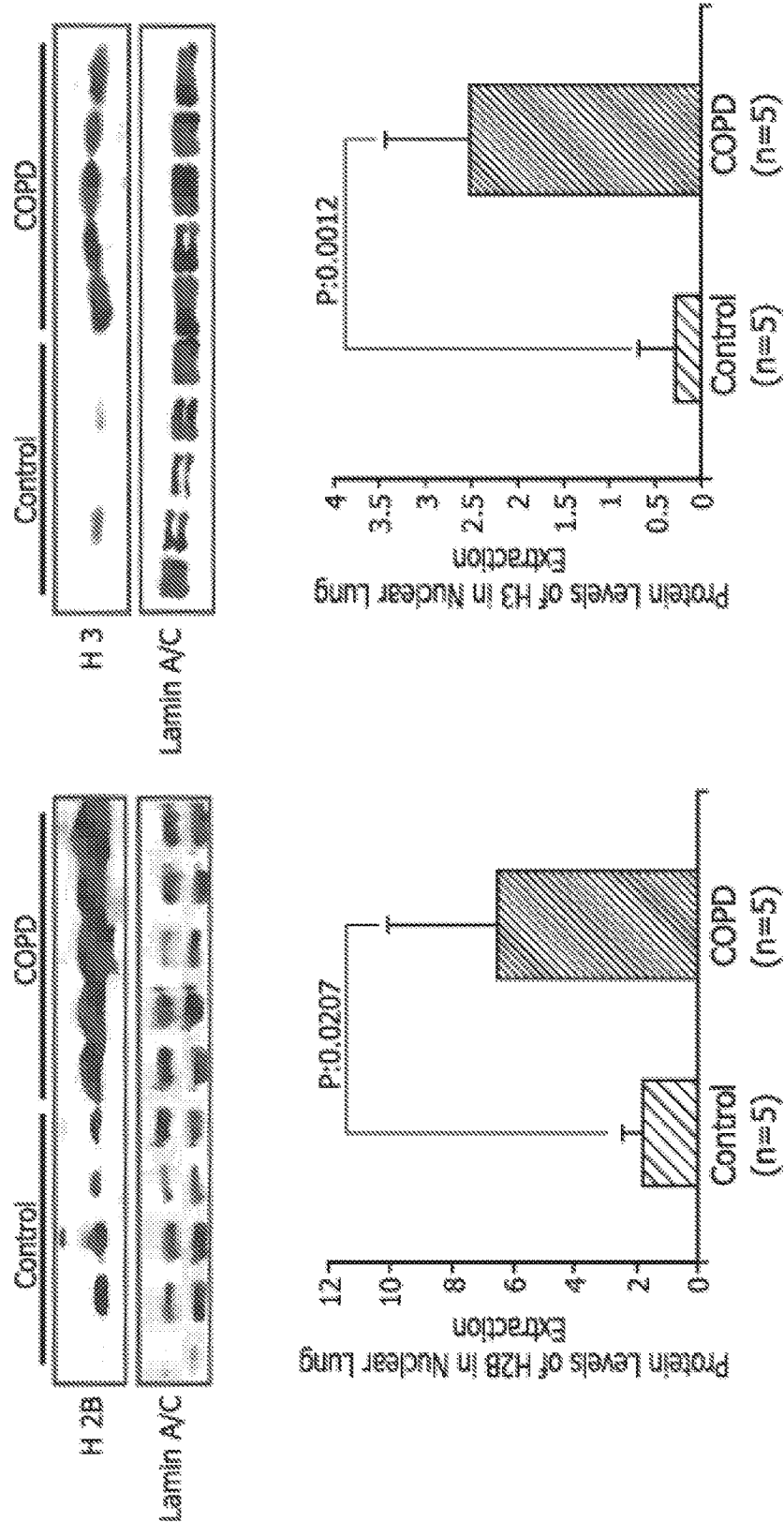
FIGS. 1A and 1B illustrate that H2B and H3 are elevated in COPD patients.

As used herein, each of the following terms has the meaning associated with it in this section.

The articles "a" and "an" are used herein to refer to one or to more than one (i.e. to at least one) of the grammatical object of the article. By way of example, "an element" means one element or more than one elements.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

The term "in vitro method," as used herein, refers to a method carried out outside of a living organism as opposed to an "in vivo method" which is a method carried out inside or on a living organism.

The term "H3.3," as used herein, refers to Histone 3.3 and all isoforms and allelic variations thereof. (SEQ ID NO: 1) (FIG. 2A) (UniprotKB Accession No. P84243)

The term "H2A," as used herein, refers to Histone 2A and all isotypes, isoforms and allelic variations thereof. e.g. Histone 2A type 1 (SEQ ID NO: 2) (UniprotKB Accession No. P0C0S8)

```
                                        (SEQ ID NO: 2)
         10         20         30         40
MSGRGKQGGK ARAKAKTRSS RAGLQFPVGR VHRLLRKGNY 50         60         70         80
AERVGAGAPV YLAAVLEYLT AEILELAGNA ARDNKKTRII 90        100        110        120
PRRLQLAIRN DEELNKLLGK VTIAQGGVLP NIQAVLLPKK

130
TESHHKAKGK
```

The term "H2B," as used herein, refers to Histone 2B and all isotypes, isoforms and allelic variations thereof. e.g. Histone 2B type 1-A (SEQ ID NO: 3) (UniprotKB Accession No. Q96A08)

```
                                        (SEQ ID NO: 3)
         10         20         30         40
MPEVSSKGAT ISKKGFKKAV VKTQKKEGKK RKRTRKESYS 50         60         70         80
IYIYKVLKQV HPDTGISSKA MSIMNSFVTD IFERIASEAS 90        100        110        120
RLAHYSKRST ISSREIQTAV RLLLPGELAK HAVSEGTKAV

TKYTSSK
``` or Histone 2B type F-S (Histone type F-S) (SEQ ID NO:4) (UniprotKB Accession No. P57053)

```
                                        (SEQ ID NO: 4)
         10         20         30         40
MPEPAKSAPA PKKGSKKAVT KAQKKDGRKR KRSRKESYSV 50         60         70         80
YVYKVLKQVH PDTGISSKAM GIMNSFVNDI FERIAGEASR 90        100        110        120
LPHYNKRSTI TSREIQTAVR LLLPGELAKH AVSEGTKAVT

KYTSAK
```

Other isotypes of H2B comprise:
H2B type 2-E (UniprotKB Accession No. Q16778)
H2B type 1-C/E/F/G/I (UniprotKB Accession No. P62807)
H2B type 1-J (UniprotKB Accession No. P06899)
H2B type 1-L (UniprotKB Accession No. Q99880)
H2B type 1-D (UniprotKB Accession No. P58876)
H2B type 1-O (UniprotKB Accession No. P23527)
H2B type 1-B (UniprotKB Accession No. P33778)
H2B type 1-H (UniprotKB Accession No. Q93079)
H2B type 1-M (UniprotKB Accession No. Q99879)
H2B type 1-N (UniprotKB Accession No. Q99877)
H2B type 1-K (UniprotKB Accession No. O60814)

H2B type F-M (UniprotKB Accession No. P0C1H6)
H2B type 3-B (UniprotKB Accession No. Q8N257)
H2B type 2-F (UniprotKB Accession No. Q5QNW6)
H2B type 2-B (UniprotKB Accession No. Q64525)
H2B type W-T (UniprotKB Accession No. Q7Z2G1)

The term "H3," as used herein, refers to Histone 3 and all isotypes, isoforms and allelic variations thereof. e.g. Histone 3.1 (Histone 3 type 1) (SEQ ID NO: 5) (UniprotKB Accession No. KB P68431)

```
                                                  (SEQ ID NO: 5)
          10         20         30         40
   MARTKQTARK STGGKAPRKQ LATKAARKSA PATGGVKKPH 50         60         70         80
   RYRPGTVALR EIRRYQKSTE LLIRKLPFQR LVREIAQDFK 90        100        110        120
   TDLRFQSSAV MALQEACEAY LVGLFEDTNL CAIHAKRVTI

130
   MPKDIQLARR IRGERA
``` or Histone 3.2 (SEQ ID NO: 6) (UniprotKB Accession No. Q71DI3)

```
                                                  (SEQ ID NO: 6)
          10         20         30         40
   MARTKQTARK STGGKAPRKQ LATKAARKSA PATGGVKKPH 50         60         70         80
   RYRPGTVALR EIRRYQKSTE LLIRKLPFQR LVREIAQDFK 90        100        110        120
   TDLRFQSSAV MALQEASEAY LVGLFEDTNL CAIHAKRVTI

130
   MPKDIQLARR IRGERA.
```

The term "H4," as used herein, refers to Histone 4 and all isotypes, isoforms and allelic variations thereof. (SEQ ID NO: 7) (UniprotKB Accession No. KB P62805)

```
                                                  (SEQ ID NO: 7)
          10         20         30         40
   MSGRGKGGKG LGKGGAKRHR KVLRDNIQGI TKPAIRRLAR 50         60         70         80
   RGGVKRISGL IYEETRGVLK VFLENVIRDA VTYTEHAKRK 90        100
   TVTAMDVVYA LKRQGRTLYG FGG.
```

As used herein, "post-translational modification" refers to any chemical modification of a polypeptide after it is produced. Commonly, a post-translational modification involves attaching at least one moiety to the polypeptide chain, however, post-translational modification can be cleavage of the polypeptide chain, proteolytic processing, the formation of disulfide bonds, and the like. Non-limiting examples of post-translational modifications include glycosylation, phosphorylation, acylation, acetylation, methylation, sulfonation, prenylation, isoprenylation, ubiquitination, biotinylation, formylation, citrullination, myristolation, ribosylation, sumoylation, gamma carboxylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, demethylation, formation of covalent cross-links, formation of cystine, formation of pyroglutamate, CPI anchor formation, hydroxylation, iodination, methylation, nitrosylation, oxidation, proteolytic processing, racemization, selenoylation, sulfation, transfer-RNA mediated addition of amino acids to proteins such as arginylation, and the like. See, for instance, Proteins—Structure and Molecular Properties, $2^{nd}$ Ed., T. E. Creighton, W.H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al, (1990) Analysis for Protein Modifications and Nonprotein Cofactors, Methods Enzymol. 182: 626-46 and Rattan et al. (1992) Protein Synthesis: Posttranslational Modifications and Aging, Ann. NY Acad. Sci. 663:48-62.

As used herein, "chronic obstructive pulmonary disease (COPD)" refers to a chronic progressive lung disease. Chronic bronchitis and emphysema are non-limiting examples of COPD. COPD can be diagnosed by pulmonary function tests and/or chest X-rays in accordance with accepted clinical practice. Clinically relevant diagnostic tests include: $FEV_1$ (the volume of air forcefully expired during the first second after taking a full breath); forced vital capacity (FVC; the total volume of air expired with maximal force); and flow-volume loops, which are simultaneous spirometric recordings of airflow and volume during forced maximal expiration and inspiration. Reductions of $FEV_1$, FVC, and the ratio of $FEV_1/FVC$ are hallmarks of airflow limitation. See Merck Manual Online for Healthcare Professionals, Pulmonary Disorders, Chronic Obstructive Pulmonary Disorder, Introduction (downloaded from www(dot)merckmanuals(dot)com/professional/sec05/ch049/ch049a(dot)html on 19 Dec. 2010). Severity of disease can be assessed on the same criteria.

"GOLD" is the abbreviation for the Global Initiative for Chronic Obstructive Lung Disease. GOLD classifications designate the severity of disease for COPD patients as shown in Table 1.

TABLE 1

| GOLD classification | Description | Criteria |
| --- | --- | --- |
| 0 | At-risk of COPD | |
| I | Mild COPD | $FEV_1/FVC < 0.7$ |
| | | $FEV_1 \geq 80\%$ predicted |
| II | Moderate COPD | $FEV_1/FVC < 0.7$ |
| | | $50\% \leq FEV1 < 80\%$ predicted |
| III | Severe COPD | $FEV_1/FVC < 0.7$ |
| | | $30\% \leq FEV1 < 50\%$ predicted |
| IV | Very severe COPD | $FEV_1/FVC < 0.7$ |
| | | FEV1 < 30% predicted or |
| | | FEV1 < 50% predicted with chronic respiratory failure |

"GOLD I-IV" are also known as "GOLD 1-4," respectively.

As used herein, "severity of COPD" refers generally to the extent of airflow limitation and optionally to associated symptoms such as chronic coughing and sputum production, as clinically defined parameters. The GOLD classifications are exemplary for classifying COPD severity.

"Increased severity of COPD" is used herein to refer to an increase in airflow limitation (e.g., increased limitation in airflow) and optionally to worsening of associated symptoms such as chronic coughing and sputum production in a COPD patient relative to a normal reference, or relative to the subject at an earlier point in time. An exemplary normal reference can be a non-smoker or an ex-smoker who does not have clinical evidence of COPD, or a population of non-smokers and/or ex-smokers who do not have clinical evidence of COPD. The normal reference can be representative of the patient with regard to approximate age, age group, body-mass index ("BMI"), gender and/or other parameters.

"At risk for developing COPD" refers to a subject having one or more risk factors for COPD. Risk factors known in the art include, but are not limited to, a history of tobacco smoking; long term exposure to one or more of organic dust, inorganic dust, chemical fumes, smoke such as from burning biomass or coal, gases, vapors and mists; and $\alpha_1$-antitrypsin deficiency.

As used herein, the term "subject" or "patient" refers to any animal (e.g., a mammal) including, but not limited to, humans and non-human primates, at risk for developing COPD or diagnosed with COPD. Typically, the terms "subject" and "patient" are used interchangeably herein in reference to a human subject.

As used herein, a "normal subject" or "control subject" refers to a subject that does not manifest clinical symptoms of COPD.

As used herein, a "normal reference" refers to a normal subject or to a population of normal subjects.

"Increased susceptibility of developing COPD" is used herein to refer to an increase in the likelihood or possibility of a subject developing COPD relative to a normal reference, or relative to the subject at an earlier point in time. An exemplary normal reference can be a non-smoker or an ex-smoker who does not have clinical evidence of COPD, or a population of non-smokers and/or ex-smokers who do not have clinical evidence of COPD. The normal reference can be representative of the patient with regard to approximate age, age group, body mass index (BMI), gender and/or other parameters.

"Sample" or "test sample" as used herein means a biological material isolated from an individual. The test sample may contain any biological material suitable for detecting the desired biomarkers, and may comprise cellular and/or non-cellular material obtained from the individual. The sample or test sample may comprise a biological fluid, blood, plasma or serum.

As used herein, a "detector molecule" is a molecule that may be used to detect a compound of interest. Non-limiting examples of a detector molecule are molecules that bind specifically to a compound of interest, such as, but not limited to, an antibody, a cognate receptor or binding partner, an aptamer, and a small molecule.

By the term "specifically binds," as used herein with respect to a detector molecule such as an antibody, is meant a detector molecule that recognizes a specific binding partner, such as an antigen, but does not substantially recognize or bind other molecules in a sample. For instance, in a sample containing H2A, an antibody that specifically binds to H2A does not substantially recognize or bind to other molecules in the sample.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody," as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

As used herein, an "immunoassay" refers to any binding assay that uses an antibody capable of binding specifically to a target molecule to detect and quantify the target molecule.

It is understood that any and all whole or partial integers between any ranges set forth herein are included herein. As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DETAILED DESCRIPTION OF THE INVENTION

COPD is characterized by lung inflammation, cell death and extensive lung tissue remodeling. However, until now methods of diagnosing or staging COPD by employing histones as markers were unknown in the art. There are also few known treatments for COPD. The present invention meets those needs.

Provided are methods for diagnosing or staging COPD by measuring histone protein levels or by detecting post-translational modifications in histone proteins. Diagnosing or staging may be conducted on a patient who is at risk for developing COPD, or someone having one or more risk factors for COPD. Risk factors known in the art include, but are not limited to, a history of tobacco smoking; long term exposure to one or more of organic dust, inorganic dust, chemical fumes, smoke such as from burning biomass or coal, gases, vapors and mists; and $\alpha_1$-antitrypsin deficiency.

Detection of Protein Levels and the Presence of Post-Translational Modifications The methods described herein rely on assessing the level of a biomarker, whose level correlates in a statistically significant manner with the diagnosis and staging of COPD, in a sample obtained from the patient. The sample may be, without limitations, a biological tissue or a biological fluid.

The sample can be selected, without limitations, from lung tissue, bronchoalveolar lavage fluid ("BALF"), peripheral whole blood, and components thereof such as blood serum ("serum") and blood plasma ("plasma"). In preferred embodiments, the sample is plasma. The sample is obtained from the subject using conventional methods in the art. For instance, one skilled in the art knows how to draw blood and how to process it in order to obtain serum and/or plasma for use in practicing the described methods. Generally speaking, the method of obtaining and storing, if necessary, the sample preferably maintains the integrity of the one or more histone biomarkers the disclosed herein such that it can be accurately quantified in the biological fluid sample.

The methods of the invention include quantitatively measuring the level of an unmodified or post-translationally modified protein biomarker such as H2A, H2B, H3, H3.3 or H4. Methods of quantitatively assessing the level of an unmodified or post-translationally modified protein in a biological fluid such as plasma are well known in the art. In some embodiments, assessing the level of an unmodified or post-translationally modified protein involves the use of a detector molecule for the biomarker. In preferred embodiments, the detector molecule is specific for either the unmodified or the post-translationally modified protein biomarker. Detector molecules can be obtained from commercial vendors or can be prepared using conventional methods in the art. Exemplary detector molecules include, but are not limited to, an antibody that binds specifically to the unmodified or post-translationally modified biomarker, a naturally-occurring cognate receptor, or functional domain thereof, for the unmodified or post-translationally modified biomarker, an aptamer that binds specifically to the unmodified or post-translationally modified biomarker, and a small molecule that binds specifically to the unmodified or post-translationally modified biomarker. Small molecules that bind specifically to an unmodified or post-translationally modified biomarker can be identified using conventional methods in the art, for instance, screening of compounds using combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. Methods for preparing aptamers are also well-known in the art.

The methods of the invention also include detecting the presence or absence of a post-translational modification in a biomarker such as, for example, H3.3, using detector molecules such as those described supra which are specific for a certain post-translationally modified biomarker.

In a preferred embodiment, the level of an unmodified or post-translationally modified biomarker is assessed using an antibody. Thus, exemplary methods for assessing the level of an unmodified or post-translationally modified biomarker in a biological fluid sample include various immunoassays, for example, immunohistochemistry assays, immunocytochemistry assays, ELISA, capture ELISA, sandwich assays, enzyme immunoassay, radioimmunoassay, fluorescence immunoassay, and the like, all of which are known to those of skill in the art. See e.g. Harlow et al., 1988, Antibodies: A Laboratory Manual, Cold Spring Harbor, N.Y.; Harlow et al., 1999, Using Antibodies: A Laboratory Manual, Cold Spring Harbor Laboratory Press, NY. Solid phase immunoassays can be particularly useful. Where two or more unmodified or post-translationally modified biomarkers are assessed, a panel of antibodies in an array format can be utilized. Custom antibody microarrays or chips can be obtained commercially.

The generation of polyclonal antibodies is accomplished by inoculating the desired animal with an antigen and isolating antibodies which specifically bind the antigen therefrom.

Monoclonal antibodies directed against one biomarker identified herein may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Human monoclonal antibodies may be prepared by the method described in U.S. patent publication 2003/0224490. Monoclonal antibodies directed against a biomarker such as H3.3 can be generated, for instance, from mice immunized with the biomarker using standard procedures as referenced herein.

For use in preparing an antibody, a biomarker may be purified from a biological source that endogenously comprises the biomarker, or from a biological source recombinantly-engineered to produce or over-produce the biomarker, using conventional methods known in the art. The amino acid sequence for the biomarker H3.3 is provided as SEQ ID NO:1. Exemplary nucleic acid sequences for the biomarkers described herein are readily available in public sequence databases, such as National Library of Medicine's genetic sequence database GenBank® (Benson et al., 2008, *Nucleic Acids Research*, 36 (Database issue):D25-30).

Nucleic acid encoding the monoclonal antibody obtained using the procedures described herein may be cloned and sequenced using technology which is available in the art, and is described, for example, in Wright et al. (1992, Critical Rev. Immunol. 12 (3,4):125-168) and the references cited therein.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory Press, Cold Spring Harbor, N.Y.).

Bacteriophage which encode the desired antibody may be engineered such that the protein is displayed on the surface thereof in such a manner that it is available for binding to the antigen against which the antibody is directed. Thus, when bacteriophage which express a specific antibody are incubated in the presence of the antigen, for instance, antigen immobilized on a resin or surface, the bacteriophage will bind to the antigen. Bacteriophage which do not express the antibody will not bind to the antigen. Such panning techniques are well known in the art and are described for example, in Wright et al., (supra). Processes, such as those described above, have also been developed for the production of human antibodies using M13 bacteriophage display (Burton et al., 1994, Adv. Immunol. 57:191-280).

The procedures just presented describe the generation of phage which encode the Fab portion of an antibody molecule. However, phage which encode single chain antibodies (scFv/phage antibody libraries) are also useful in preparing Fab molecules useful in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA. Synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105) may also be used to prepare an antibody useful in the practice of the invention.

Other methods for assessing the level of a protein include chromatography (e.g., HPLC, gas chromatography, liquid chromatography), capillary electrophoresis and mass spectrometry (e.g., MS, MS-MS). For instance, a chromatography medium comprising a cognate receptor for the biomarker, an aptamer that binds specifically to the biomarker, or a small molecule that binds specifically to the biomarker can be used to substantially isolate the biomarker from the sample of biological fluid.

The level of substantially isolated protein can be quantitated directly or indirectly using a conventional technique in the art such as spectrometry, Bradford protein assay, Lowry protein assay, biuret protein assay, or bicinchoninic acid protein assay, as well as immunodetection methods.

The level of an unmodified or post-translationally modified biomarker in a biological fluid sample can be normalized. For instance, the level can be normalized to another component of the fluid sample, whose level is independent of whether the patient suffers from COPD. It is well within the skill of the skilled artisan to select a suitable component for normalization. An exemplary, but non-limiting, component for normalization is the IgG light chain.

Kits

A kit is envisaged for practicing every method disclosed herein. The following is a description of a kit useful for diagnosing COPD comprising measuring the level of extracellular H2B, H3, H3.3 or H4 protein in a test sample of a patient and comparing the level of extracellular H2B, H3, H3.3 or H4 protein to the extracellular level of H2B, H3, H3.3 or H4 protein respectively in a control sample, wherein an elevated level of extracellular H2B, H3, H3.3 or H4 protein in the test sample of the patient as compared to the level of extracellular H2B, H3, H3.3 or H4 protein respectively in the control sample indicates that the patient suffers from COPD. The description is not intended to be limiting and should not be construed that way.

Kits can comprise a detector molecule that binds to H2B, H3, H3.3 or H4. For example, the kit can comprise an antibody, an antibody derivative, or an antibody fragment that binds specifically with a biomarker protein of the invention. The kit may alternatively comprise an aptamer or small molecule that binds specifically to a biomarker of the invention. Such kits may also comprise a plurality of antibodies, antibody derivatives, or antibody fragments wherein the plurality of such antibody agents binds specifically with H2B, H3, H3.3 or H4, or a fragment of H2B, H3, H3.3 or H4.

For antibody-based kits, the kit can comprise, for example: (1) a first antibody (e.g., attached to a solid support) that specifically binds to H2B, H3, H3.3 or H4; and, optionally, (2) a second, different antibody that specifically binds to either H2B, H3, H3.3 or H4 or the first antibody and is conjugated to a detectable label.

The kit can further comprise components necessary for detecting the detectable label (e.g., an enzyme or a substrate). Optionally, the kit comprises at least one negative control containing H2B, H3, H3.3 or H4 at a level of about the extracellular level of H2B, H3, H3.3 or H4 which is present in a test sample of a healthy subject. Optionally, the kit also includes at least one positive control containing H2B, H3, H3.3 or H4 at a level of about the extracellular level of H2B, H3, H3.3 or H4 which is present in a test sample of a COPD patient.

Furthermore, the kit can optionally include instructional material for use of the kit in the diagnosis of COPD. Such instructions may comprise instructions to: detect the presence of or assess the level of H2B, H3, H3.3 or H4.

The instructional material may comprise a publication, a recording, a diagram, or any other medium of expression which can be used to communicate the usefulness of the method of the invention in the kit for diagnosis of COPD in a patient. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

The kit may optionally further include at least one sample container for containing a test sample obtained from the patient. Kits for practice of the invention may also comprise, e.g., buffering agents, preservatives, or protein stabilizing agents. Each component of the kit can be enclosed within an individual container and all of the various containers can be within a single package, along with instructions for interpreting the results of the assays performed using the kit.

The following is a description of a kit useful for staging COPD comprising measuring the level of H2B, H3 or H4 protein in a test sample of a patient; and comparing the level of H2B, H3 or H4 protein to the level of H2B, H3 or H4 protein in a sample from a control healthy person without COPD, a GOLD 0 control, a GOLD I control, a GOLD II control, a GOLD III control or a GOLD IV control, determining which control has the most similar level of H2B, H3 or H4 protein to that of the patient, and assigning to the patient the stage of the control with the most similar level of H2B, H3 or H4 protein to that of the patient. The description is not intended to be limiting and should not be construed that way.

Kits can comprise a detector molecule that binds to H2B, H3 or H4. For example, the kit can comprise an antibody, an antibody derivative, or an antibody fragment that binds specifically with a biomarker protein of the invention. The kit may alternatively comprise an aptamer or small molecule that binds specifically to a biomarker of the invention. Such kits may also comprise a plurality of antibodies, antibody derivatives, or antibody fragments wherein the plurality of such antibody agents binds specifically with H2B, H3 or H4, or a fragment of H2B, H3 or H4.

For antibody-based kits, the kit can comprise, for example: (1) a first antibody (e.g., attached to a solid support) that specifically binds to H2B, H3 or H4; and, optionally, (2) a second, different antibody that specifically binds to either H2B, H3 or H4 or the first antibody and is conjugated to a detectable label.

The kit can further comprise components necessary for detecting the detectable label (e.g., an enzyme or a substrate). Optionally, the kit comprises at least one negative control containing H2B, H3 or H4 at a level of about the extracellular level of H2B, H3 or H4 which is present in a biological sample or in a biological fluid sample of a healthy subject, a GOLD 0 control, a GOLD I control, a GOLD II control, a GOLD III control or a GOLD IV control.

Furthermore, the kit can optionally include instructional material for use of the kit in the assessment of COPD staging. Such instructions may comprise instructions to: detect the presence of or assess the level of H2B, H3 or H4.

The instructional material may comprise a publication, a recording, a diagram, or any other medium of expression which can be used to communicate the usefulness of the method of the invention in the kit for staging of COPD in a patient, as described above.

The kit may optionally further include other elements such as containers and buffers, as described above.

The following is a description of a kit useful for diagnosing COPD comprising detecting the level of an H3.3 protein with at least one post-translational modification from a biological sample of a patient, comparing the level of an H3.3 protein with at least one post-translational modification to the level of an H3.3 protein with at least one post-translational modification from a biological sample of a healthy control, wherein an elevated number of post-translational modifications of H3.3 in the patient as compared to the healthy control indicates that the patient suffers from COPD. The description is not intended to be limiting and should not be construed that way.

Kits can comprise a detector molecule that binds to an H3.3 protein with at least one post-translational modification. For example, the kit can comprise an antibody, an antibody derivative, or an antibody fragment that binds specifically with a biomarker protein of the invention. The kit may alternatively comprise an aptamer or small molecule that binds specifically to a biomarker of the invention. Such kits may also comprise a plurality of antibodies, antibody derivatives, or antibody fragments wherein the plurality of such antibody agents bind specifically with an H3.3 protein with at least one post-translational modification, or a fragment of an H3.3 protein with at least one post-translational modification.

For antibody-based kits, the kit can comprise, for example: (1) a first antibody (e.g., attached to a solid support) that specifically binds to an H3.3 protein with at least one post-translational modification; and, optionally, (2) a second, different antibody that binds to either an H3.3 protein with at least one post-translational modification or the first antibody and is conjugated to a detectable label.

The kit can further comprise components necessary for detecting the detectable label (e.g., an enzyme or a substrate). Optionally, the kit comprises at least one negative control containing H3.3 protein at a level of about the extracellular level of an H3.3 protein with at least one post-translational modification which is present in a biological sample or in a biological fluid sample of a healthy subject. Optionally, the kit also includes at least one positive control containing an H3.3 protein with at least one post-translational modification at a level of about the extracellular level of an H3.3 protein with at least one post-translational modification which is present in a biological sample or in a biological fluid sample of a COPD patient.

Furthermore, the kit can optionally include instructional material for use of the kit in the diagnosis of COPD. Such instructions may comprise instructions to: detect the presence of or assess the level of an H3.3 protein with at least one post-translational modification.

The instructional material may comprise a publication, a recording, a diagram, or any other medium of expression which can be used to communicate the usefulness of the method of the invention in the kit for diagnosis of COPD in a patient based on the level of an H3.3 protein with at least one post-translational modification, as described above.

The kit may optionally further include other elements such as containers and buffers, as described above.

The following is a description of a kit useful for diagnosing COPD by a method comprising detecting at least one post-translational modification of an H3.3 protein from a biological sample of a patient at position 10, 15, 28, 38, 43, 80, 107, 111, 116, or 121 of SEQ ID NO:1, wherein the presence of at least one said post-translational modification indicates that the patient suffers from COPD. In a preferred embodiment, the kit is useful for diagnosing COPD by a method comprising detecting at least one post-translational modification of an H3.3 protein from a biological sample of a patient at position 10, 15, 28, 38, 43, 80, 107 or 116 of SEQ ID NO:1. The description is not intended to be limiting and should not be construed that way.

Kits can comprise a detector molecule that binds to post-translationally modified H3.3. For example, the kit can comprise an antibody, an antibody derivative, or an antibody fragment that binds specifically with a biomarker protein of the invention. The kit may alternatively comprise an aptamer or small molecule that binds specifically to a biomarker of the invention. Such kits may also comprise a plurality of antibodies, antibody derivatives, or antibody fragments wherein the plurality of such antibody agents binds specifically with post-translationally modified H3.3, or a fragment of post-translationally modified H3.3.

For antibody-based kits, the kit can comprise, for example: (1) a first antibody (e.g., attached to a solid support) that specifically binds to post-translationally modified H3.3; and, optionally, (2) a second, different antibody that specifically binds to either post-translationally modified H3.3 or the first antibody and is conjugated to a detectable label.

The kit can further comprise components necessary for detecting the detectable label (e.g., an enzyme or a substrate). Optionally, the kit includes at least one positive control containing post-translationally modified H3.3.

Furthermore, the kit can optionally include instructional material for use of the kit in the diagnosis of COPD. Such instructions may comprise instructions to: detect the presence of or assess the level of post-translationally modified H3.3.

The instructional material may comprise a publication, a recording, a diagram, or any other medium of expression which can be used to communicate the usefulness of the method of the invention in the kit for diagnosis of COPD in a patient, as described above.

The kit may optionally further include other elements such as containers and buffers, as described above.

Methods of Treatment for COPD

Provided is a method of treating COPD by administering to a patient suffering from COPD an agent that degrades H3.3 or targets H3.3 for degradation or inhibits the function of H3.3 or prevents the toxicity caused by H3.3. In some embodiments, the agent is DNase I, activated protein C or antibody to H3.3. Methods for administration and the appropriate dosages and pharmaceutical compositions of the agent that degrades H3.3 or targets H3.3 for degradation or inhibits the function of H3.3 or prevents the toxicity caused by H3.3 will be known to a person skilled in the art. A method for administrating the agent can be any method usable in this field of technology, including aerosol delivery, intra-arterial injection, dripping, intravenous injection, intramuscular injection, subcutaneous injection, intradermal injection, oral administration, mucosal administration, and transdermal administration.

Detection of Anti-Histone Antibodies.

Provided is a method for diagnosing COPD comprising determining the levels of anti-H2B, anti-H3, anti-H3.3 or anti-H4 antibodies in a patient, determining the levels of anti-H2B, anti-H3, anti-H3.3 or anti-H4 antibodies in a control, and comparing the level of anti-H2B, anti-H3, anti-H3.3 or anti-H4 antibodies to the level of anti-H2B, anti-H3, anti-H3.3 or anti-H4 antibodies respectively in an ex-smoker control, wherein an elevated level of anti-H2B, anti-H3, anti-H3.3 or anti-H4 antibodies in the patient as compared to the level of anti-H2B, anti-H3, anti-H3.3 or anti-H4 antibodies in the control indicates that the patient suffers from COPD. In preferred embodiments, the anti-H3.3 antibodies specifically recognize post-translationally modified H3.3, wherein the post-translational modifications are characteristic of COPD. In some embodiments, the control is from an ex-smoker who may be at risk of, but does not have COPD, such as a GOLD 0.

In order to perform the immunological assay, the histone peptides that said anti-histone antibodies specifically bind to can be adsorbed or covalently linked or modified with a carrier to bind them to a solid support (e.g. chips, microspheres, gold, polystyrene, reactor vessel or wells, microtiter plate). In a first step of the assay method, the sample of biological fluid to be analyzed is placed in contact and incubated with the preferred histone peptide linked on the solid support. Any anti-histone antibodies that are possibly present in the sample are thus specifically bound to the preferred peptide, producing an antigen/antibody complex. The anti-histone antibodies to be detected in the immunoassay may be IgG immunoglobulins, or any other class of immunoglobulins. The evaluation of the presence and the quantization of the antigen/antibody complex can be performed with a spectroscopic, a piezoelectric or an electrochemical biosensor.

In a preferred embodiment, the above described method is an ELISA immunoassay in which an indicator antibody, such as an anti-human IgG, is conjugated to an enzyme and is added to measure the antibody titer by spectroscopy.

EXAMPLES

Example 1. Elevation of Core Histone Proteins in COPD

Overview

Gene expression is regulated epigenetically by a variety of nuclear proteins, including histones and transcription factors. Accordingly, we characterized protein expression levels in pooled samples of a nuclear-enriched cell fraction using label-free, gel electrophoresis mass spectroscopy.

Clinical Study Material

Lungs were obtained by the region's transplant network, Gift of Life Inc under a protocol approved by the Temple University Institutional Review Board from five ex-smokers (GOLD 0), and five ex-smokers with severe COPD (GOLD 4) (Table 2A). Mean age, smoking history and time from smoking cessation were similar in COPD subjects and controls (Table 2B).

TABLE 2A

Discovery Group

| GOLD | Subj # | Gender | Age | Pk-Yrs | Stp-Yrs | FEV1% | FEV1.FVC % | DLCO/VA % |
|---|---|---|---|---|---|---|---|---|
| 0 | 291090 | F | 23 | NA | NA | 104 | 90 | NA |
| 0 | 119716 | M | 59 | 58 | 15 | 70 | 80 | NA |
| 0 | 298520 | F | 69 | NA | NA | 97 | 70 | 99 |
| 0 | 41 | F | 75 | 30 | 16 | 112 | 80 | 64 |
| 0 | 59 | M | 49 | 30 | 4 | 85 | 72 | 75 |
| IV | 192361 | F | 50 | 70 | 2 | 12 | 20 | NA |
| IV | 132625 | F | 63 | 120 | 10 | 23 | 30 | 17 |
| IV | 174 | M | 48 | 60 | 4 | 47 | 49 | 75 |
| IV | 8 | F | 59 | 42 | 6 | 16 | 42 | 63 |
| IV | 33 | M | 56 | 35 | 7 | 16 | 24 | 39 |

TABLE 2B

Subject Demographics
Discovery Group (n = 10): Subject Demographics

| GOLD | Subject # | Gender | Race | Age | PkYrs | Quit Time (Mo) | FEV1% | FEV1/FVC% |
|---|---|---|---|---|---|---|---|---|
| GOLD 0 | 5 | 3F/2M | 2AA/3C | 59 (13.3) | 38.6 (11.6) | 10.6 (4.8) | 93.6 (16.5) | 78.4 (7.9) |
| GOLD IV | 5 | 3F/2M | 2AA/3C | 55.2 (6.2) | 65.4 (33.5) | 5.8 (3.0) | 22.8 (14.1) | 33 (12.2) |

| Group | Subject # | Gender F/M | Race AA/H/C | Age Mean (SD) | PkYrs Mean (SD) | Quit Time (Mo) Mean (SD) | FEV1% Mean (SD) | FEV1/FVC% Mean (SD) |
|---|---|---|---|---|---|---|---|---|
| NS | 14 | 6F/8M | 2AA/12C | 45.4 (16.7) | 0 | N/A | N/A | N/A |
| S | 9 | 3F/6M | 2AA/7C | 40.1 (14.3) | 14.4 (11.3) | 0 | N/A | N/A |

TABLE 2B-continued

Subject Demographics
Discovery Group (n = 10): Subject Demographics

| GOLD 0 | 11 | 4F/7M | 1AA/10C | 63.4 (7.7) | 54.4 (36.3) | 81.9 (165.5) | 81.9 (11.8) | 81.8 (5.7) |
|---|---|---|---|---|---|---|---|---|
| GOLD I-III | 14 | 6F/8M | 3AA/11C | 67.7 (6.2) | 53.6 (29.2) | 92.4 (135.4) | 64.1 (19.1) | 51.5 (15.4) |
| GOLD IV | 24 | 12F/12M | 5AA/19C | 57.5 (5.9) | 49.7 (25.3) | 86.8 (65.6) | 20.1 (4.8) | 31.8 (9.8) |
| IPF/PPH/Sar | 9 | 5F/4M | 3AA/6C | 55.4 (8.5) | 15.5 (19.6) | 88 (103.9) | 51.2 (13.7) | 75.6 (10.7) |

All lungs were obtained from beating heart donors, immediately placed in sterile, ice-cold preservation medium (Hall et al. 1994), and shipped to a laboratory on ice within 12 hours of collection. Radiologically and macroscopically normal appearing regions were selected for this study. The region selected, usually an entire lobe, was slowly inflated using a cannula inserted into the supplying airway to instill a 1:1 mix of cryo-embedding medium (Cryomatrix®, Thermo Electron Corp.) and 50% sucrose in distilled water.

Portions of the inflated organ were then frozen by suspension in liquid nitrogen fumes for 20-25 minutes, as previously described (Gonzalez et al. 1996), then stored at −80° C. until used. Samples of frozen tissues were cut into 0.1×1×1 cm blocks and embedded in OCT (Tissue Tek®). Sample sections (6 μm) were cut from each block using a cryostat at −20° C. then stained with hematoxylin and eosin for inspection. Since whole lung tissue is comprised of at least 6 major cell types, considerable effort was made to obtain approximately equal amounts of lung parenchyma, small airways and pulmonary vessels. In this regard, the amount (~1 cm$^3$) and location (peripheral tissue extending to include the pleural surface) of the sample were standardized.

Subject Groups:
Study Population

Lung tissue, bronchoalveolar lavage fluid (BALF) and plasma samples were obtained from 15 subjects with GOLD stage 4 COPD and 15 subjects without COPD, i.e., GOLD 0, normal non-smokers and normal active smokers.

Demographics, smoking history, co-morbidities and cause of death are shown in Table 2B. Ex-smokers with severe COPD had higher heavy smoke exposure than ex-smokers (65±33 SE pack years, range 35-120 yrs, and 39±16 SE pack years, range 30-58 yrs, for ex-smokers with severe COPD and ex-smokers, respectively). The ex-smokers had normal lung function as indicated by FV1.FVC % of ≥70. In contrast, the ex-smokers with severe COPD had impaired lung function FV1.FVC % of ≤49.

The two groups appeared evenly matched in terms of age and gender. All were Caucasians except for one African American in the smoker group. Subjects in all 2 groups had co-morbidities, but these appeared to be similar.

Figure 6A:
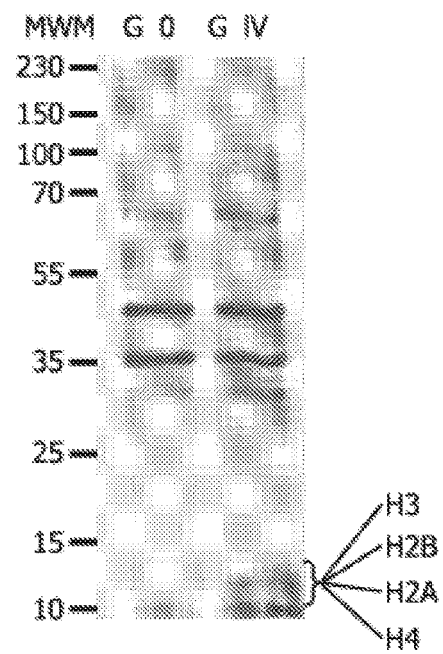
FIGS. 6A and 6B illustrate that core histone proteins are elevated in COPD.
Figure 6B:
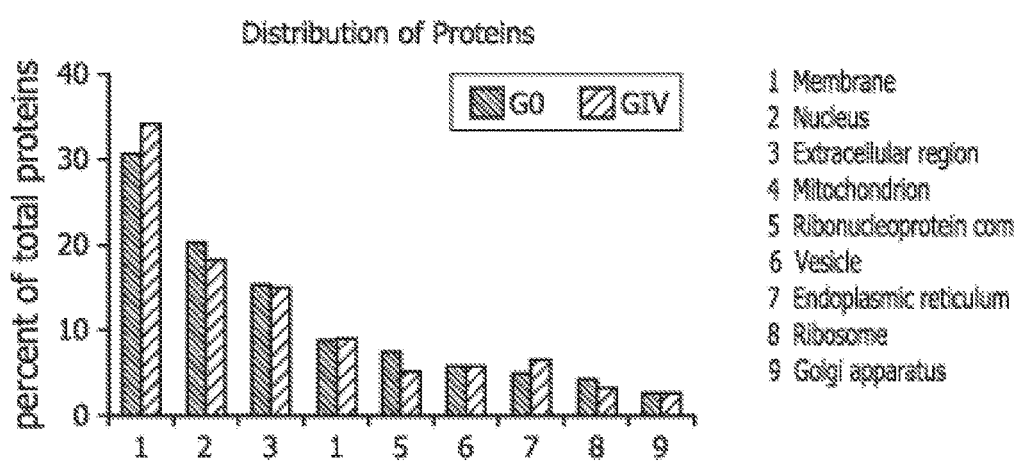

Nuclear Protein Fractionation:

In order to reduce red blood cell contamination of samples, the frozen lung tissue was dipped twice in 1.5 ml centrifuge tubes containing 1×PBS. Cytosolic and nuclear proteins were extracted from the tissue using a hypotonic lysis buffer consisting of 0.1×PBS, 0.1% Triton X-100 and 1× protease inhibitor (Pierce Halt PI cocktail 100×). After incubation on ice for 10 min to allow cells to swell, the sample was homogenized for 2 min. Centrifugation at 10,000 g for 15 min separated the cytosolic fraction (supernatant) from the nuclei-enriched fraction (pellet). The cytosolic fraction was stored at −80° C. The nuclear fraction was washed twice with the hypotonic lysis buffer using the same centrifugation protocol then nuclear proteins were extracted from the nuclei by a lysis buffer (1×PBS pH 7.9, SDS 1%, EDTA 5 mM, 50 mM DTT, and 1× protease inhibitor cocktail) through 2 min of sonication (20 sec on 20 sec off) at 4° C., centrifuged at 16,000 g for 10 min. The final supernatant (nuclear extract) was collected for storage at −80° C. The specificity of this subcellular fraction method was supported by protein identification results and analysis of distribution of proteins (FIG. 6B).

In-Gel Trypsin Digestion:

Samples containing a total of 30 μg of nuclear proteins were diluted with Laemmli sample buffer (BioRad) containing 5% β-mercaptoethanol. The mixture was heated for 5 min at 95° C. and loaded onto 10-14% polyacrylamide gel. One dimension SDS PAGE separation was performed using a mini Protean II system (BioRad) at 200 V for 45 min. Bands were visualized with SimplyBlue SafeStain and lanes were sliced into 15 sections which were diced into ~2×4 mm. Proteins in gel pieces were reduced by 30 min incubation at 37° C. with 50 mM ammonium bicarbonate buffer containing 10 mM DTT. Proteins in the gel were alkylated by 30 min incubation in the dark at RT with 50 mM ammonium bicarbonate buffer containing 50 mM iodoacetamide. After destaining with 50% (v/v) acetonitrile in 50 mM bicarbonate and dehydration with pure acetonitrile, the gel pieces were covered with approximately 40 μl 12.5 μg/μl trypsin in 50 mM ammonium bicarbonate buffer. Incubation for digestion, peptide extraction, and sample cleanup and desalting using "Ziptips" were as previously described.

GeLC-MS:

Peptides were dried in a vacuum centrifuge then resolubilized in 30 μl of 0.1% (vol/vol) trifluoroacetic acid/$H_2O$. Peptide samples were loaded onto 2 μg capacity peptide traps (CapTrap; Michrom Bioresources) and separated using a C18 capillary column (15 cm 75 μm, Agilent) with an Agilent 1100 LC pump delivering mobile phase at 300 nl/min. Gradient elution using mobile phases A (1% acetonitrile/0.1% formic acid, balance $H_2O$) and B (80% acetonitrile/0.1% formic acid, balance $H_2O$) was as follows (percentages for B, balance A): linear from 0 to 15% at 10 min, linear to 60% at 60 min, linear to 100% at 65 min. The nanoelectrospray ionization (nanoESI) tandem MS was performed using a HCT Ultra ion trap mass spectrometer (Bruker). ESI was delivered using distal-coating spray Silica tip (ID 20 μM, tip inner ID 10 μM, New Objective) at a spray voltage of −1300 V. Using an automatic switching between MS and MS/MS modes, MS/MS fragmentation was performed on the two most abundant ions on each spectrum using collision-induced dissociation with active exclusion (excluded after two spectra, and released after 2 min). The complete system was fully controlled by HyStar 3.1 software.

Data Analysis:

Mass spectra processing was performed using Bruker Daltonics esquire 6.1 DataAnalysis (Version 3.4). The generated de-isotoped peak list was submitted to an in-house Mascot server 2.2 for searching against the Swiss-Prot database (version 56.6 of 16 Dec. 2008, 405506 sequences). Mascot search parameters were set as follows: species, *Homo sapiens* (20413 sequences); enzyme, trypsin with maximal 1 missed cleavage; fixed modification, cysteine carboxymethylation; variable modification, methionine oxidation; 0.45 Da mass tolerance for precursor peptide ions; and 0.6 Da for MS/MS fragment ions. All peptides matches were filtered using an ion score cutoff of 10.

Labeled Free Quantitation:

Statistical validation of Mascot results were performed using the ProteinProphet tool of Trans-Proteomic Pipeline (TPP) software. As a result, probability values were generated for protein identification based on MS/MS data. Those proteins with ProteinProphet probabilities >0.90 were subjected to labeled free quantitation analysis using Absolute Protein Expression (APEX) tool. Differentially expressed proteins were analyzed by functional annotation clustering using the Database for Annotation, Visualization and Integrated Discovery (DAVID) v6.7.

Western Blot Analysis:

Protein samples (20 μg) were separated by 10-14% gradient SDS-PAGE then transferred to a nitrocellulose membrane in a semi-dry blotting chamber (Biorad) at 10 V for 3 hours. The membrane was blocked with 5% powdered milk in phosphate-buffer saline solution (pH 7.4) containing 0.05% Tween-20 (TBS/T) then probed with antibodies that had been diluted 1:1000 for primary antibodies (anti-H2B and anti-H3, anti-lamin A/C and anti-β-actin, all mouse monoclonal) and 1:10.000 for secondary antibody (HRP-conjugated goat anti-mouse). Membranes were incubated with primary antibodies overnight at 4° C., washed, and then incubated with HRP-conjugated goat anti-mouse at room temperature for 1 hour. A Western Lightening Chemiluminescence Plus kit (Pelkin Elkins) for HRP was used according to the manufacturer's instruction and signals were captured onto X-ray film.

Results Mass Spectroscopy:

Mass spectroscopy analysis of the pooled nuclear fractions from the ex-smokers with severe COPD (i.e., GOLD 4 category; n=5) and ex-smokers who served as controls (i.e., GOLD 0; n=5) identified 17 differentially expressed proteins in severe COPD compared to controls (Table 4, GO-GIV section). Of considerable interest, H3 was up-regulated 8 fold in COPD compared to controls (p=3.34×10$^{-5}$) In addition, H2B and H4 were up-regulated approximately 2 fold. In fact, increased expression of the core histones was apparent on the 1D gel of the pooled lung samples (FIG. 6A).

TABLE 3

H3.3 modifications in COPD

| G0 | Intensity | Mr(expt) | Mr(calc) | Score | Peptide† | SEQ ID NO: |
|---|---|---|---|---|---|---|
| 1 | 172617 | 1027.34 | 1027.61 | 40 | R.KQLATKacAAR.K | 8 |
| 2 | 2049354 | 3450.34 | 3450.71 | 102 | R.FQSAAIGALQEASEAYLVGLFEDTNLCcaAIHAKme.R | 9 |
| 3 | 786579 | 1069.84 | 1069.62 | 65 | R.KacQLATKacAAR.K | 10 |
| 4 | 13203808 | 1348.80 | 1348.70 | (28) | R.EIAQDFKTDmeLR.F | 11 |
| 5 | 6255877 | 1391.78 | 1391.69 | (29) | R.EIAQdeDmeFKacTDLR.F | 12 |
| 6 | 3792373 | 1448.75 | 1448.73 | 49 | R.EIAQDFKglTDLR.F | 13 |
| 7 | 5679177 | 3439.24 | 3438.65 | 35 | R.FQdeSAAIGALQdeEASEAYLVGLFEmeDTNdeLCAIHAKac.R | 14 |

| GIV | Intensity | Mr(expt) | Mr(calc) | Score | Peptide† | SEQ ID NO: |
|---|---|---|---|---|---|---|
| 1 | 704419 | 1504.37 | 1504.88 | 45 | R.KdiSAPSTGGVKKdiPHR.Y | 15 |
| 2 | 1158315 | 1348.25 | 1348.70 | 43 | R.EIAQDFKmeTDLR.F | 16 |
| 3 | 12160767 | 3449.52 | 3450.71 | 86 | R.FQSAAIGALQEASEAYLVGLFEmeDmeTNLCniAIHA trimethylation of lysine at position 80;.R | 17 |
| 4 | 432467 | 984.29 | 984.54 | 57 | R.KacSTGGKacAPR.K | 18 |
| 5 | 1477098 | 1027.34 | 1027.61 | 53 | R.KQLATKacAAR.K | 19 |
| 6 | 1419091 | 1069.29 | 1069.62 | (44) | R.KacQLATKacAAR.K | 20 |
| 7 | 10169535 | 3435.41 | 3435.70 | 112 | R.FQSAAIGALQEASEAYLVGLFEDTNLCAIHAKacme.R | 21 |
| 8 | 22322976 | 3449.44 | 3449.72 | (82) | R.FQSAAIGALQEASEAYLVGLFEmeDTNLCAIHAKacme.R | 22 |
| 9 | 2435156 | 859.34 | 859.49 | 38 | K.RVTIMoxPK.D | 23 |
| 10 | 297772 | 958.39 | 958.54 | 52 | R.KdiSAPSTGGVK.K | 24 |
| 11 | 3759162 | 1348.26 | 1348.70 | 28 | R.EIAQDFKmeTDLR.F | 25 |
| 12 | 6308548 | 1059.78 | 1059.62 | 49 | R.YRdiPGTVALR.E | 26 |
| 13 | 808426 | 1069.91 | 1069.62 | 65 | R.KacQLATKacAAR.K | 27 |
| 14 | 4964585 | 1448.80 | 1448.73 | 52 | R.EIAQDFKglTDLR.F | 28 |
| 15 | 7104697 | 3438.33 | 3437.67 | 43 | R.FQSAAIGALQdeEASEAYLVGLFEmeDTNdeLCAIHAKac.R | 29 |

TABLE 3 -continued

H3.3 modifications in COPD

| 16 | 15146324 | 1348.82 | 1348.70 | 47   | R.EIAQDFKmeTDLR.F     | 30 |
| 17 | 6238915  | 1391.82 | 1390.75 | (33) | R.EIAQDFKtrTDmeLR.F   | 31 |

†Tryptic peptides are shown. The tryptic peptide sequence is shown between the periods, which indicate the trypsin cleavage sites. The amino acid residues immediately flanking the tryptic peptide in the H3.3 sequence are shown.

KEY:
Oxidation M: Mox
Acetyl K: Kac
Methyl D: Dme
Dimethyl K: Kdi
Methyl E: Eme
Trimethyl K: Ktr
Methyl K: Kme
GlyGlyK: Kgl (Diglycine is left at sites of ubiquitinylation after trypsin digestion.)
Methyl (C-term): me
Carbamidomethyl C: Cca
Nitrosyl C: Cni
Deamidated N: Nde
Dimethyl R: Rdi
Deamidated Q: Qde

TABLE 4

Differential expression of Lung Nuclear Proteins in Chronic Obstructive Pulmonary Disease

| | ACC | Gene Name | Protein Probability (x) GO | Protein Probability (x) GIV | Percent Coverage GO | Percent Coverage GIV | Tot Num Peps GO | Tot Num Peps GIV | APEX Score (y) GO | APEX Score (y) GIV | APEX Fold (z) | Differential Expression | Description |
|---|---|---|---|---|---|---|---|---|---|---|---|---|---|
| GO-GIV | P00367 | DHE3_HUMAN | 1 | 1 | 7.5 | 22.2 | 6 | 13 | 0.0095 | 0.0266 | 2.8 | Up | Glutamate dehydrogenase 1, mitochondrial |
| | P02671-1 | FIBA_HUMAN | 0.99 | 1 | 2.5 | 8.5 | 3 | 8 | 0.0068 | 0.0234 | 3.5 | Up | Isoform 1 of Fibrinogen alpha chain |
| | P02679-1 | FIBG_HUMAN | 1 | 1 | 11 | 20.4 | 7 | 17 | 0.0189 | 0.0592 | 3.1 | Up | Isoform Gamma-B of Fibrinogen gamma chain |
| | P05023-1 | AT1A_HUMAN | 0.99 | 1 | 1.9 | 7.1 | 3 | 9 | 0.0045 | 0.0175 | 3.9 | Up | Isoform Long of Sodium/potassium-transporting ATPase subunit alpha-1 |
| | P05164-1 | PERM_HUMAN | 1 | 1 | 8.5 | 16.5 | 5 | 14 | 0.0070 | 0.0253 | 3.6 | Up | Isoform H17 of Myeloperoxidase |
| | P05362 | ICAM1_HUMAN | 0.99 | 1 | 4.5 | 16.2 | 2 | 8 | 0.0049 | 0.0257 | 5.2 | Up | Intercellular adhesion molecule 1 |
| | P08670 | VIME_HUMAN | 1 | 1 | 58.6 | 54.5 | 212 | 115 | 0.1631 | 0.1140 | 1.4 | Down | Vimentin |
| | P12111-1 | CO6A3_HUMAN | 1 | 1 | 8.7 | 4.6 | 61 | 19 | 0.0291 | 0.0117 | 2.5 | Down | Isoform 1 of Collagen alpha-3(VI) chain |
| | P21980-1 | TGM2_HUMAN | 1 | 1 | 7.3 | 12.1 | 7 | 13 | 0.142 | 0.0339 | 2.4 | Up | Isoform 1 of Protein-glutamine gamma-glutamyltransferase 2 |
| | P26038 | MOES_HUMAN | 1 | 1 | 20.5 | 22.2 | 9 | 19 | 0.0110 | 0.0298 | 2.7 | Up | Moesin |
| | P35579-1 | MYH9_HUMAN | 1 | 1 | 18.1 | 23.4 | 55 | 66 | 0.0219 | 0.0338 | 1.5 | Up | Isoform 1 of Myosin-9 |
| | P35580-1 | MYH10_HUMAN | 1 | 1 | 8.2 | 10.8 | 18 | 25 | 0.0097 | 0.0174 | 1.8 | Up | Isoform 1 of Myosin-10 |
| | P57053 | H2BFS_HUMAN | 1 | 1 | 41.3 | 29.4 | 21 | 31 | 0.0918 | 0.1745 | 1.9 | Up | Histone H2B type F—S |
| | P62805 | H4_HUMAN | 1 | 1 | 58.3 | 58.3 | 23 | 33 | 0.0821 | 0.1518 | 1.8 | Up | Histone H4 |
| | P68431 | H31_HUMAN | 1.00 | 1 | 18.7 | 31.9 | 3 | 19 | 0.0136 | 0.1108 | 8.2 | Up | Histone H3.1 |
| | Q9NZN4 | EHD2_HUMAN | 1 | 1 | 32.4 | 12 | 22 | 6 | 0.0285 | 0.0100 | 2.8 | Down | EH domain-containing protein 2 |
| | Q9Y490 | TLN1_HUMAN | 1 | 1.00 | 4.7 | 0.9 | 13 | 2 | 0.0085 | 0.0017 | 5.1 | Down | Talin-1 |
| GO Only | P68371 | TBB2C_HUMAN | 1 | | 27.6 | | 23 | | | | | | Tubulin beta-2C chain |
| | Q9BQE3 | TBA1C_HUMAN | 1 | | 20.9 | | 10 | | | | | | Tubulin alpha-1C chain |
| | P08123 | CO1A2_HUMAN | 1 | | 2.4 | | 8 | | | | | | Collagen alpha-2(I) chain |
| | P13747 | HLAE_HUMAN | 1 | | 12 | | 5 | | | | | | HLA class 1 histocompatability antigen, alpha chain E |
| | Q00610-1 | CLH1_HUMAN | 1 | | 2.9 | | 5 | | | | | | Isoform 1 of Clathrin heavy chain 1 |
| | P02743 | SAMP_HUMAN | 1 | | 20.2 | | 4 | | | | | | Serum amyloid P-component |
| | P10909 | CLUS_HUMAN | 1 | | 8.9 | | 4 | | | | | | Clusterin |
| | P35232 | PHB_HUMAN | 1 | | 10.7 | | 4 | | | | | | Prohibitin |
| | P55083 | MFAP_HUMAN | 0.96 | | 7.5 | | 4 | | | | | | Microfibril-associated glycoprotein 4 |
| | Q14344 | GNA13_HUMAN | 1 | | 8 | | 4 | | | | | | Guanine nucleotide-binding protein subunit apha-13 |

TABLE 4-continued

Differential expression of Lung Nuclear Proteins in Chronic Obstructive Pulmonary Disease

| | ACC | Gene Name | Protein Probability (x) | | Percent Coverage | | Tot Num Peps | | APEX Score (y) | | APEX Fold (z) | Differential Expression | Description |
| --- | --- | --- | --- | --- | --- | --- | --- | --- | --- | --- | --- | --- | --- |
| | | | GO | GIV | GO | GIV | GO | GIV | GO | GIV | | | |
| | Q6DN03 | H2BC_HUMAN | 0.90 | | 15.2 | | 4 | | | | | | Putative histone H2B type 2-C |
| | O00264 | PGRC1_HUMAN | 1 | | 14 | | 3 | | | | | | Membrane-associated progesterone receptor component 1 |
| | O60504-1 | VINEX_HUMAN | 1 | | 10 | | 3 | | | | | | Isoform Alpha of Vinexin |
| | O94833-2 | BPAEA_HUMAN | 0.94 | | 0.3 | | 3 | | | | | | Isoform 6 of Bullous pemphigoid antigen 1, isoforms 6/9/10 |
| | P04275 | VWF_HUMAN | 0.99 | | 1.1 | | 3 | | | | | | von Willebrand factor |
| | P18077 | RL35A_HUMAN | 0.94 | | 8.2 | | 3 | | | | | | 60S ribosomal protein L35a |
| | P21291 | CSRP1_HUMAN | 1.00 | | 15.7 | | 3 | | | | | | Cysteine and glycine-rich protein 1 |
| | P51991-1 | ROA3_HUMAN | 1 | | 7.1 | | 3 | | | | | | Isoform 1 of Heterogeneous nuclear ribonucleoprotein A3 |
| | Q13185 | CBX3_HUMAN | 1 | | 13.7 | | 3 | | | | | | Chromobox protein homolog 3 |
| | Q9NYL9 | TMOD3_HUMAN | 1 | | 6 | | 3 | | | | | | Tropomodulin-3 |
| | Q9Y624 | JAM1_HUMAN | 1 | | 17.7 | | 3 | | | | | | Junctional adhesion molecule A |
| GIV Only | P30483 | 1B45_HUMAN | | 1 | | 18.2 | | 9 | | | | | HLA class 1 histocompatibility antigen, B-45 alpha chain |
| | Q71U36 | TBA1A_HUMAN | | 1 | | 10 | | 7 | | | | | Tubulin alpha-1A chain |
| | P63244 | GBLP_HUMAN | | 1 | | 25.3 | | 5 | | | | | Guanine nucleotide-binding protein subunit beta-2-like 1 |
| | P01877 | IGHA2_HUMAN | | 1.00 | | 5.6 | | 4 | | | | | Ig alpha-2 chain C region |
| | P09493-1 | TPM1_HUMAN | | 1 | | 20.6 | | 4 | | | | | Isoform 1 of Tropomyosin alpha-1 chain |
| | P00167-1 | CYB5_HUMAN | | 1 | | 43.9 | | 3 | | | | | Isoform 1 of Cytochrome b5 |
| | P02730 | B3AT_HUMAN | | 1 | | 5 | | 3 | | | | | Band 3 anion transport protein |
| | P04217 | A1BG_HUMAN | | 1 | | 6.3 | | 3 | | | | | Alpha-1B-glycoprotein |
| | P05109 | S10A8_HUMAN | | 1 | | 28 | | 3 | | | | | Protein S100-A8 |
| | P06702 | S10A9_HUMAN | | 1 | | 24.6 | | 3 | | | | | Protein S100-A9 |
| | P10809 | CH60_HUMAN | | 1 | | 8 | | 3 | | | | | 60 kDa heat shock protein, mitochondrial |
| | P20160 | CAP7_HUMAN | | 1 | | 11.2 | | 3 | | | | | Azurocidin |
| | P35221-1 | CTNA1_HUMAN | | 0.92 | | 1.3 | | 3 | | | | | Isoform 1 of Catenin alpha-1 |
| | P45880-1 | VDAC2_HUMAN | | 0.91 | | 4.2 | | 3 | | | | | Isoform 1 of Voltage-dependent anion-selective channel protein 2 |
| | P55072 | TERA_HUMAN | | 1.00 | | 3.6 | | 3 | | | | | Transitional endoplasmic reticulum ATPase |
| | P62158 | CALM_HUMAN | | 1 | | 20.8 | | 3 | | | | | Calmodulin |
| | Q13011 | ECH1_HUMAN | | 1.00 | | 11.3 | | 3 | | | | | Delta(3,5)-Delta(2,4)-dienoyl-CoA isomerase, mitochondrial |
| | Q14108 | SCRB2_HUMAN | | 0.97 | | 5.1 | | 3 | | | | | Lysosome membrane protein 2 |
| | Q14643-1 | ITPR1_HUMAN | | 0.96 | | 0.6 | | 3 | | | | | Isoform 1 of Inositol 1,4,5-trisphosphate receptor type 1 |
| | Q16777 | H2A2C_HUMAN | | 1.00 | | 34.9 | | 3 | | | | | Histone H2A type 2-C |
| | Q5SSJ5-1 | HP1B3_HUMAN | | 1.00 | | 11.9 | | 3 | | | | | Isoform 1 of Heterochromatin protein 1-binding protein 3 |

(X): Error rate <= 0.005
(y): False Positive Rate <= 0.0374
(z): Significant change in expression level p <= 0.05

Results Western Blotting:

To determine histone expression in the nuclear fractions from individual subjects used to form the pooled samples, Western blotting was performed. Whole lung lysates were obtained from the five individual COPD subjects and five of the ex-smoking subjects comprising the pooled sample. Both H2B and H3 levels were greater in all five COPD subjects compared to the control groups (FIG. 1A; $p<0.02$).

Example 2. H3 is Elevated in COPD

Figure 1B:
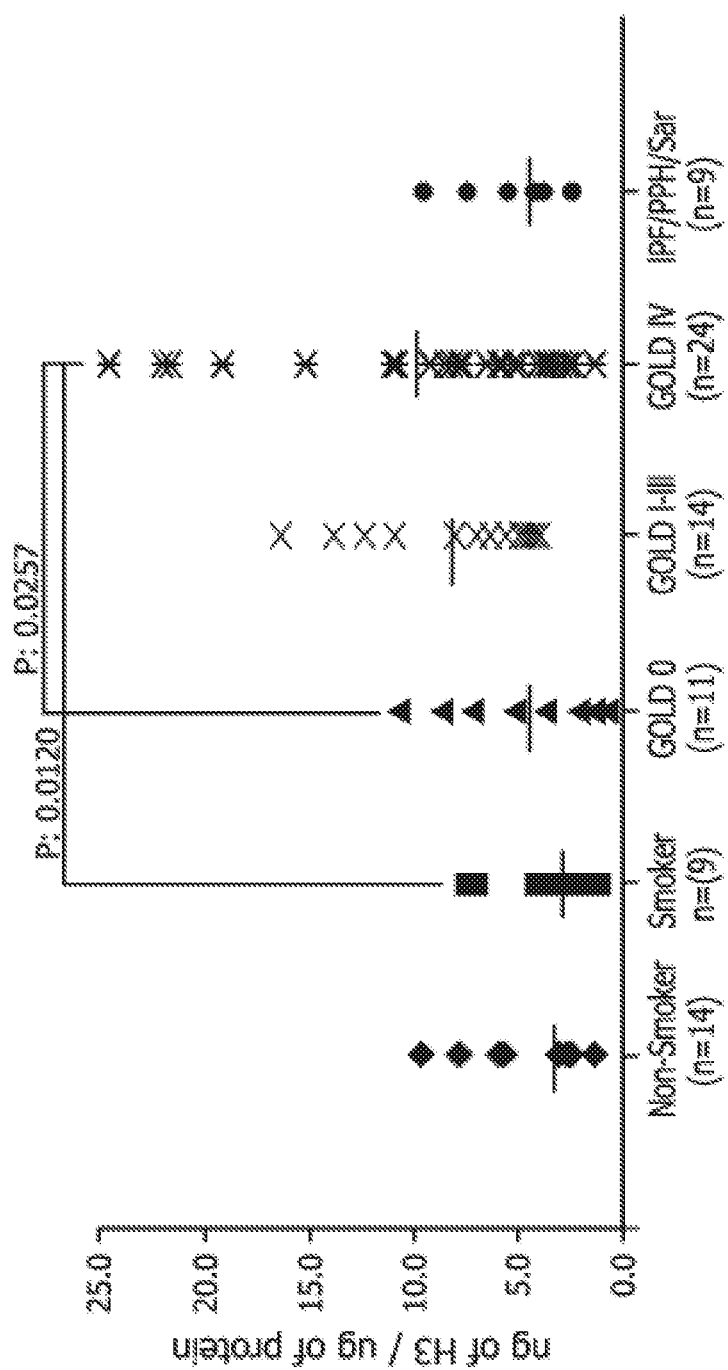

In order to extend these findings to a larger study group ("validation group"), to determine the effect on early stages of COPD, i.e., GOLD 1, 2 and 3, and to determine the specificity for COPD, an ELISA was developed to evaluate H3 levels. Subject demographics of the validation group are shown in Table 2B. FIG. 1B presents a comparison of H3 levels in GOLD 4 (n=24) and GOLD 1, 2 and 3 (n=12) to control groups consisting of non-smokers (never smoked) (n=14), Gold 0 (ex-smokers) (n=11), smokers (n=9), and patients with other lung inflammatory diseases, i.e., sarcoidosis (n=3), idiopathic pulmonary fibrosis (n=3) and pulmonary hypertension (n=3). The mean H3 levels were elevated in GOLD 4 (10 ng/µg protein) as compared to ex-smokers (5 ng/µg protein), smokers (3 ng/µg protein), healthy never smokers and other lung inflammatory diseases (5 ng/µg protein). The fact that H3 expression was greater in ex-smokers with COPD than active smokers without COPD indicates that results are not explainable by an effect of smoking per se.

Example 3. Post-Translational Modifications of Core Histones in COPD

Mass spectroscopy post-translational analysis of the pooled samples described above was performed.

Post-Translational Modifications Identification:

Modification occurrences were analyzed specifically for histone proteins using the same program and database as described above for data analysis except for some search parameters: maximal 3 missed cleavage, with variable modification: Acetyl (K), Acetyl (Protein N-term), Carbamidomethyl (C), Methyl (C-term), Methyl (DEK), Dimethyl (RK), Trimethyl (K), Nitrosylation (C), Oxidation (M), Phospho (ST), Phospho (Y), Ubiquitinylation (K); 0.60 Da mass tolerance for precursor peptide ions; and 0.9 Da for MS/MS fragment ions.

Figure 2A:
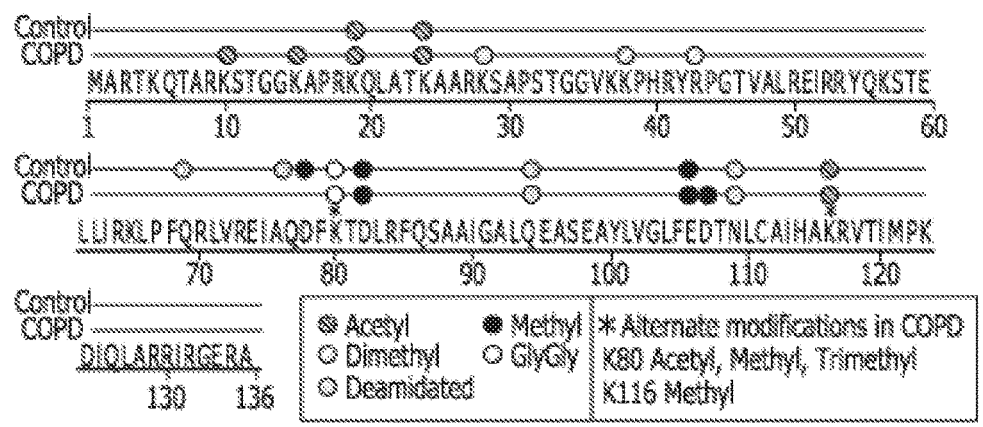
FIGS. 2A-2C illustrate H3.3 post-translational modification in COPD patients.

Results:

Several unique modifications were identified in severe COPD compared to control ex-smokers (Table 3 and FIG. 2A). H3.3 demonstrated extensive lysine acetylation and methylation in both the amino and carboxy terminal regions in severe COPD but not controls. In COPD, lysines (K) were acetylated at K10, K15, K19, K24, K80, and K116; di-methylated at K28 and K38; and mono-methylated at K80 and K116. In addition, arginine (R) dimethylation (R43), three asparate (D) and glutamate (E) methylations (D82, E106, D107), methionine oxidation (M121), and cysteine nitrosylation (C111) were identified.

Figure 2C:
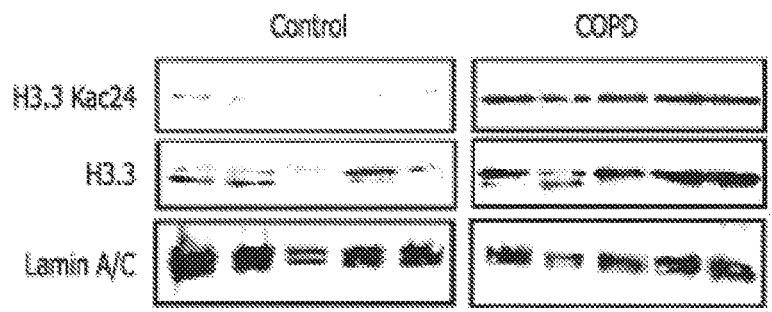
Figure 2B:
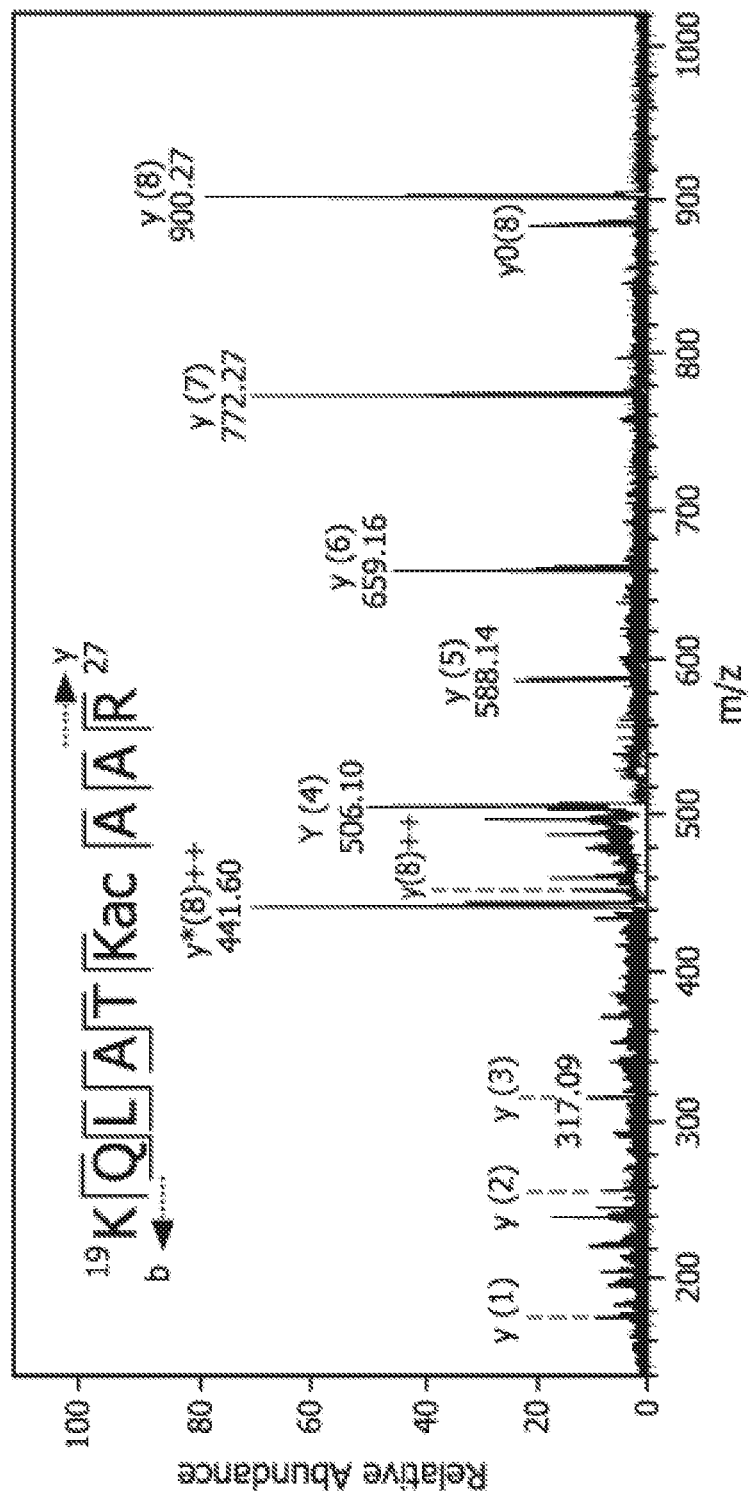

H3.3 peptide containing K24Ac (H3.3Kac24; aa 19-27 of SEQ ID No. 1; SEQ ID No. 32) was identified using doubly charged precursor ion (m/z=441.60) (FIG. 2B). The presence of H3.3Kac24 was confirmed by Western blotting, and was shown to be up-regulated in COPD as compared to the control (FIG. 2C). H3.3 was also shown to be up-regulated in COPD as compared to the control. Lamin A/C was used as an internal control.

Example 4. Presence of Extracellular Histones in the Airway in COPD

Extra-cellular histones exert biological effects. Accordingly, the presence of extra-cellular H3 in the lung was assessed by immunohistochemistry using the anti-H3 antibody used for Western blotting, above.

Immunohistochemestry of H2B and H3 in Lungs of COPD Patients:

Randomly selected tissue blocks were taken from the subpleural parenchyma (avoiding areas affected by tumor in patients who underwent lung resection for nodules) of four very severe COPD and four controls ex-smokers (GOLD 0). Samples were fixed in formalin, embedded in paraffin wax, and processed for immunohistochemical analysis of H2B with a monoclonal antibody at 1 ug per ml.

Figure 3:
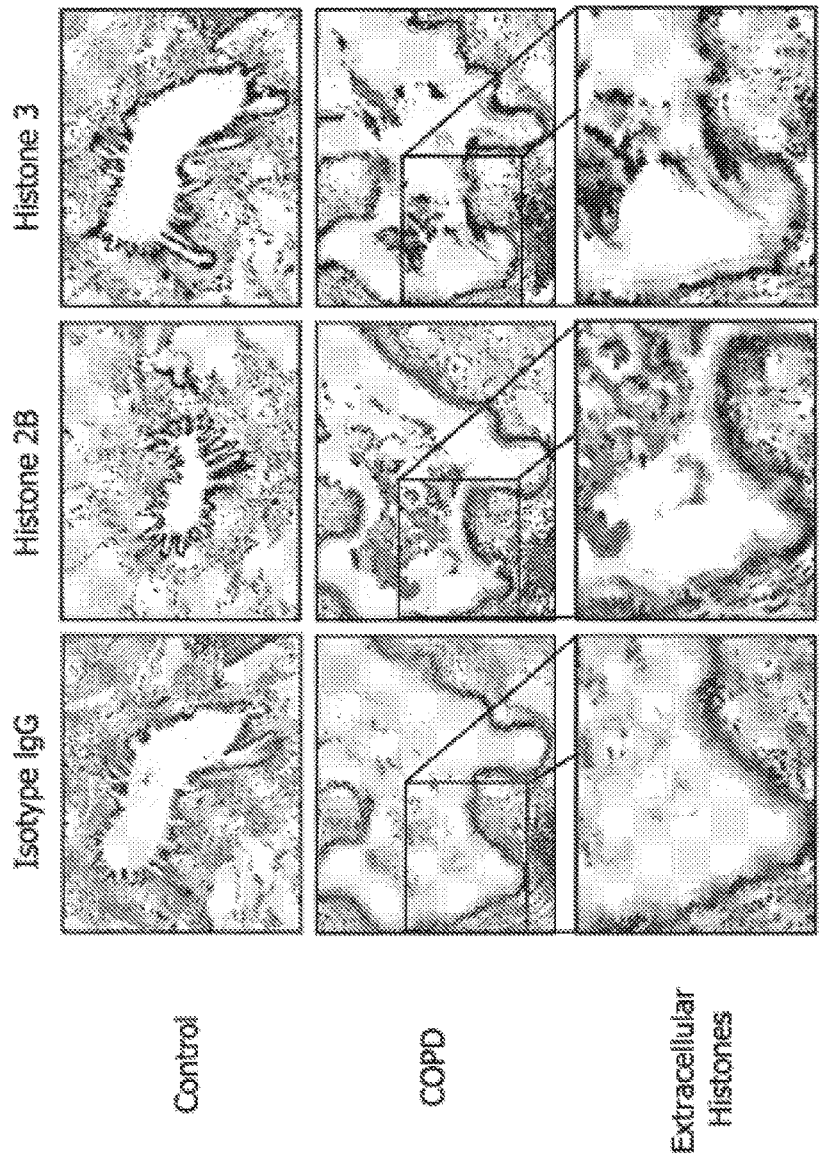
FIG. 3 illustrates expression of H2B and H3 in lung tissue. Immunohistochemical analysis of the lungs of COPD subjects showing the presence of H2B and H3 extracellularly in the lumen of airway inside of the plug of mucus together with cell debris, and the free histones are attached to the cilia of the epithelial cells. Some monocyte cells, which have very dense staining in the nucleus but stain barely in the cytoplasm, were found in the parenchyma surrounding a clog of cells and nude nucleus. The bottom row of micrographs is expanded from the corresponding boxes in the middle row of micrographs.

Results:

The results of the immunohistochemical analysis of extracellular H3 appear in FIG. 3. All cell nuclei demonstrated H3 immunoreactivity. Of interest, H3 staining was also present in mucus plugs in the airway lumen as well as in cell debris attached to the cilia of airway epithelial cells in severe COPD (n=4). In addition, monocytic cells also demonstrated cytoplasmic as well as nuclear staining for H3 in severe COPD. In contrast, H3 immunoreactivity was present in control subjects in lung cell nuclei only (n=4). These data indicate that H3 is present extra-cellularly as well as intra-cellularly in the airways and lung parenchyma of subjects with COPD.

The potential source of extra-cellular histones in the lung in COPD was not determined in this study but several potential explanations are possible. While not wishing to be bound by any one theory, core histones, H2A, H2B, H3 and H4, are exposed on the cell surface very early in the process of apoptosis and subsequently found in the extranuclear space (Gabler et al., 2003). Accordingly, increases in core histone in the lung in COPD may be a result of the heightened apoptosis of lung structural and inflammatory cells (Agusti, 2005; Demedts et al., 2006). In fact, in COPD, heightened apoptosis has been demonstrated for neutrophils in expectorated sputum, and alveolar pneumocytes and pulmonary artery endothelial cells in lung tissues (Kasahara et al., 2000; Makris et al., 2009; Yokohori et al., 2004).

Of interest, clearance of apoptotic cells by alveolar macrophages is impaired in COPD suggesting that retention of apoptotic material in the lung may be an additional mechanism for the increase in core histones observed in COPD. In fact, the impaired clearance of apoptotic cells by alveolar macrophages in COPD has been linked to activation of the RhoA-Rho kinase pathway (Richens et al., 2009).

Example 5. Detection of H3 in Cell-Free Bronchoalveolar Fluid in COPD

Given the presence of increased amounts of H3 in the lung in COPD and the presence of extracellular H3 in advanced COPD, we sought to determine if this histone were detectable in BALF in subjects with milder COPD. Accordingly, we obtained BALF from stable COPD subjects with mild to moderate disease (GOLD 1 and 2; n=12). Normal, non-smoking subjects (n=12) served as controls.

H3 in Bronchoalveolar Lavage Fluid (BALF) of COPD Patient:

The presence of H3 was evaluated in the supernatant of 2 ml of BALF from 5 healthy controls and 5 COPD patients. In brief, the total BALF was centrifuged at 2000 rpms for 10 minutes at 4 degrees, the pellet of cells were frozen and the proteins of the supernatant were concentrated by acetone precipitation, the total pellet was resuspended in 50 ul of laemmli buffer in order to run a Western blot using a monoclonal antibody against H3.

Example 6. Detection of H3 in Plasma in COPD

Because H3 was present in BALF, we also sought to determine if it was secreted into the systemic circulation.

Histones in Plasma of COPD Patient:

Immunoprecipitation against H2B and H3 was performed to determinate their presence in plasma of 5 healthy smokers and 5 COPD patients. 1 ug of each monoclonal antibody was use to interact with 60 ul of Pan mouse IgG Dynabits® for 24 h at 4°. The bits were washed twice and diluted in 1 ml with PBS-Tween 0.1%, 100 ul of bits were add to 500 ul of plasma from each subject of the Healthy smokers and COPD patients, after 24 h of incubation at 4 degrees the bits were washed three times (PBS-Tween 0.1%) and boiled in Laemmli buffer 5× for 5 minutes to evaluate the presence of H2B and H3 by Western blot.

Figure 4A:
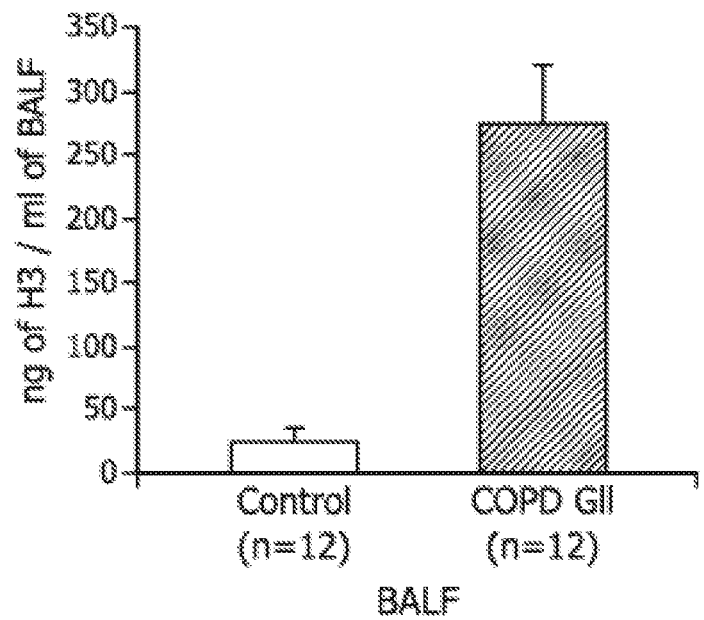
FIGS. 4A and 4B illustrate H3 in BALF and plasma of COPD patients.

Results:

H3 was increased in the BALF supernatant 12 COPD subjects by 6 folds as compared to normal non-smokers (FIG. 4A Bar graph). In contrast, H2B which was up-regulated to a lesser extent in the lung (i.e., 2 fold) than H3 (i.e., 8 fold) was not detected in either COPD or controls (data not shown).

Figure 4B:
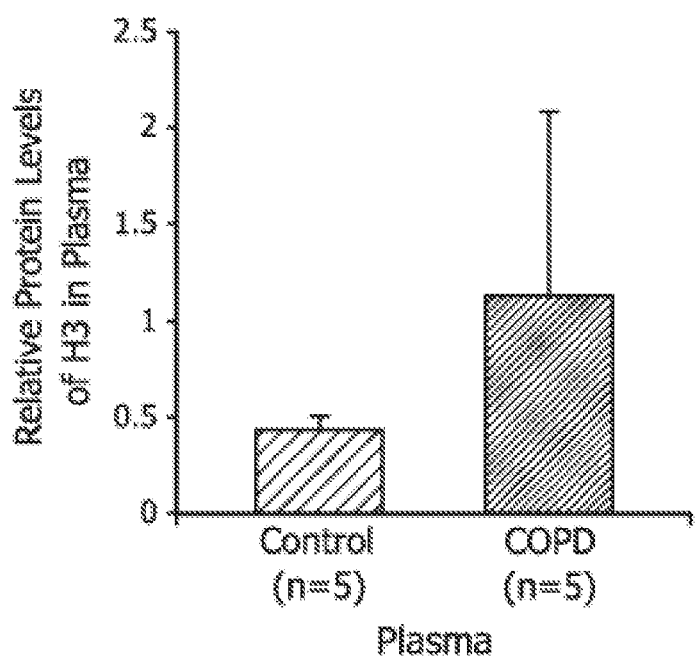

In fact, H3 was present 2 fold higher in the plasma of COPD subjects (n=5) compared with the normal active smokers (n=5) (FIG. 4B). H2B was not detected in the plasma of any of the subjects.

Example 7. Histones Induce Airway Epithelial Cell Apoptosis

Previous studies indicate that histones in the extra-cellular milieu induce apoptosis of human pulmonary endothelial cells. We, therefore, assessed the effects of a mix of histones (i.e., H1, H2A, H2B, H3 and H4) on the viability of cultured human airway epithelial cells. Histone concentrations used to assess airway epithelial cell cytotoxicity in this study were based on blood H3 concentrations present in both experimental and clinical sepsis.

HBEC Culture and Histones Cytotoxicity Assays:

Primary HBEC were extracted from broncoepithelial airway of healthy patients by brush bronchoscopy. Epithelial cells were cultured in 100-mm tissue culture dishes in Bronchial Epithelial Cell Growth medium BEGM® (Lonza), in 5% CO2 at 37° C. Cells were grown to 80% confluence before study. At the time of study, medium was replaced with medium containing a mix of histones purified from calf thymus (Sigma) at the concentration and time indicated for each experiment. Cell damage was determined by the incorporation on the cell surface of fluorescence Annexin V and measured by flow cytometry (BD FACSCalibur™) or 96 well fluorescent reader (Victor 5.0).

Figure 5A:
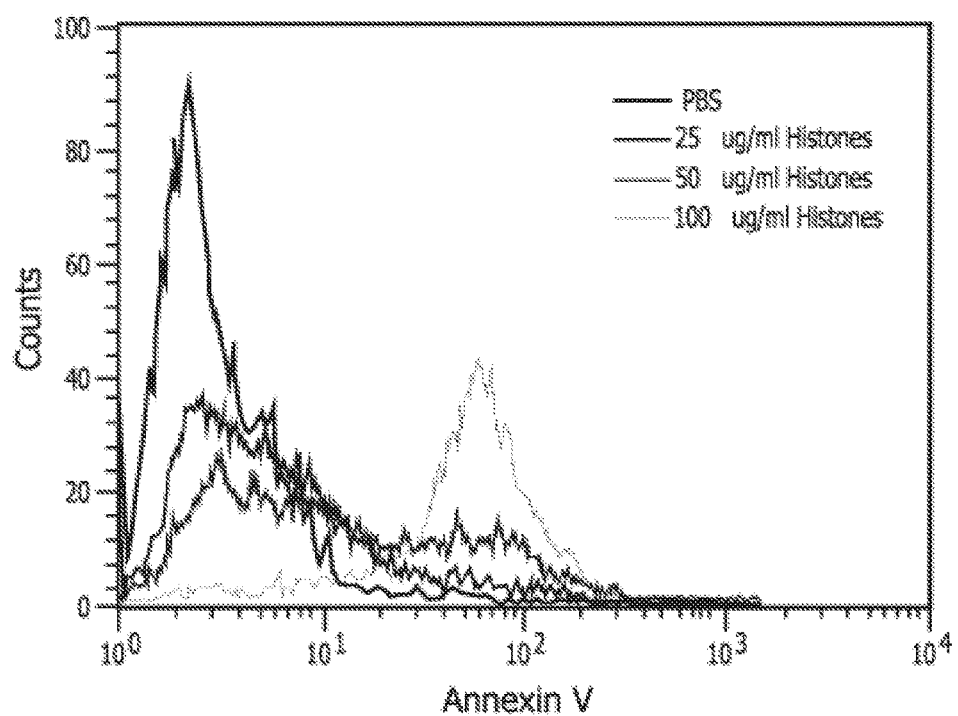
FIGS. 5A-5D illustrate that histones induce apoptosis in vitro in human bronchio-epithelial cells (HBEC) and correlate with increased apoptosis in COPD.
Figure 5B:
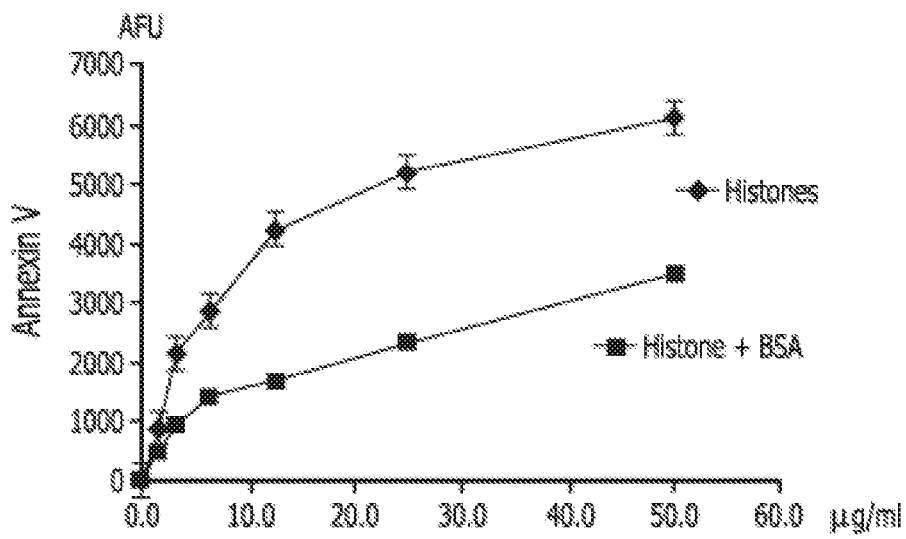
Figure 5B:
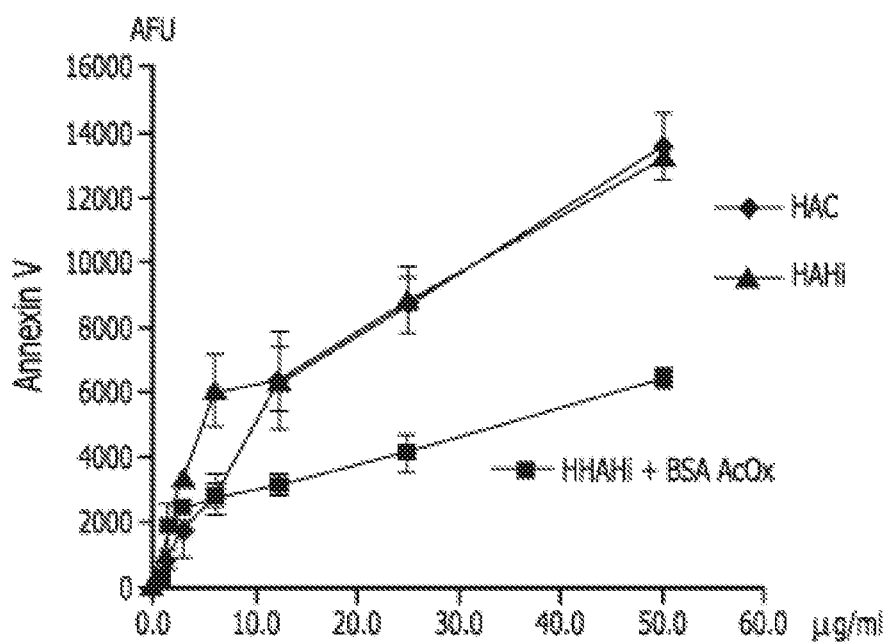
Figure 5C:
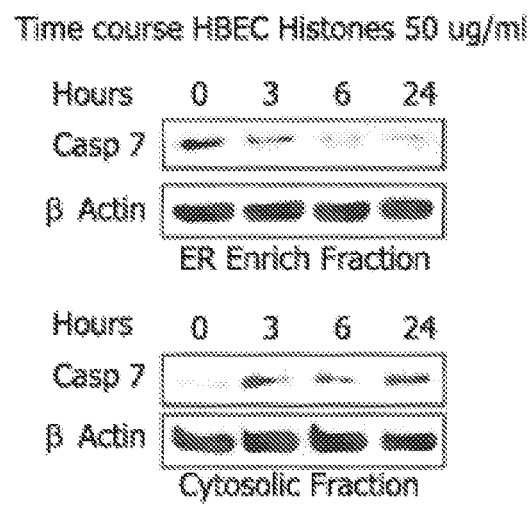
Figure 5D:
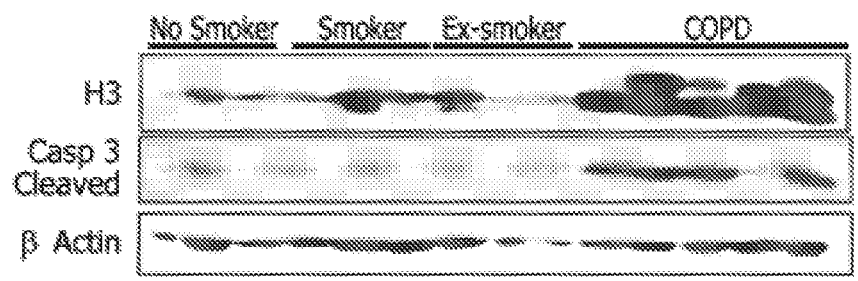

Results:

Histones dose-dependently increased Annexin V expression assessed by flow cytometry (FIGS. 5A and 5B; p<0.01 by repeated measures ANOVA). As has been previously described in sepsis, histones also rapidly (i.e., <3 hours) increased caspase 7 translocation from ER to cytoplasm indicating activation of the caspase pathway of cell apoptosis in human airway epithelial cells (FIG. 5 C).

The effects of histones on apoptosis can be reversed by blood proteins (Pemberton et al., 2010). Accordingly, we assessed the effects of a 4 fold molar excess of bovine serum albumin (BSA) on Annexin V expression at 24 hours. BSA significantly (p<0.05) inhibited histone-induced Annexin V expression but did not eliminate completely histone-induced cytotoxicity. These results with BSA are in agreement with prior studies on histone cytotoxicity in pulmonary endothelial cells (Pemberton et al., 2010; Xu et al., 2009).

Apoptosis of endothelial and epithelial cells has been proposed as a mechanism in the development of COPD (Demedts et al., 2006). Apoptosis interferes with lung maintenance and repair, which is necessary to overcome the sustained injury imposed by cigarette smoke (Godtfredsen et al., 2008). Histones in the lung extra-cellular space were biologically active since they induced dose- and time-dependent caspase activation and apoptosis of human airway epithelial cells. Moreover, similar to our results, free core histones induced apoptosis of cultured human pulmonary artery endothelial cells (Xu et al., 2009). In fact, studies in another lung disease, i.e., ARDS induced by sepsis, have found core histones in the blood and these histones contribute to lung damage and death during sepsis. That is, in a mouse model of sepsis, free core histones derived from apoptotic cells and neutrophil extra-cellular traps induced neutrophil migration into the lung, endothelial cell vacuolation, intra-alveolar hemorrhage and macro-microvascular thombosis (Xu et al., 2009).

The disclosures of each and every patent, patent application, and publication cited herein are hereby incorporated herein by reference in their entirety.

One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

REFERENCES

Agusti, A. G. (2005). COPD, a multicomponent disease: implications for management. Respir Med 99, 670-682.

Barnes, P. J. (2009a). Histone deacetylase-2 and airway disease. Ther Adv Respir Dis 3, 235-243.

Barnes, P. J. (2009b). Role of HDAC2 in the pathophysiology of COPD. Annual review of physiology 71, 451-464.

Barnes, P. J. (2009c). Targeting the epigenome in the treatment of asthma and chronic obstructive pulmonary disease. Proc Am Thorac Soc 6, 693-696.

Bhavsar, P., Ahmad, T., and Adcock, I. M. (2008). The role of histone deacetylases in asthma and allergic diseases. J Allergy Clin Immunol 121, 580-584.

Demedts, I. K., Demoor, T., Bracke, K. R., Joos, G. F., and Brusselle, G. G. (2006). Role of apoptosis in the pathogenesis of COPD and pulmonary emphysema. Respir Res 7, 53.

Gabler, C., Blank, N., Winkler, S., Kalden, J. R., and Lorenz, H. M. (2003). Accumulation of histones in cell lysates precedes expression of apoptosis-related phagocytosis signals in human lymphoblasts. Ann N Y Acad Sci 1010, 221-224.

Godtfredsen, N. S., Lam, T. H., Hansel, T. T., Leon, M. E., Gray, N., Dresler, C., Burns, D. M., Prescott, E., and Vestbo, J. (2008). COPD-related morbidity and mortality after smoking cessation: status of the evidence. Eur Respir J 32, 844-853.

Gonzalez, S., Hards, J., van Eeden, S., and Hogg, J. C. (1996). The expression of adhesion molecules in cigarette smoke-induced airways obstruction. Eur Respir J 9, 1995-2001.

Hall, S. M., Komai, H., Reader, J., and Haworth, S. G. (1994). Donor lung preservation: effect of cold preservation fluids on cultured pulmonary endothelial cells. Am J Physiol 267, L508-517.

Kasahara, Y., Tuder, R. M., Taraseviciene-Stewart, L., Le Cras, T. D., Abman, S., Hirth, P. K., Waltenberger, J., and Voelkel, N. F. (2000). Inhibition of VEGF receptors causes lung cell apoptosis and emphysema. J Clin Invest 106, 1311-1319.

Kawasaki, H., and Iwamuro, S. (2008). Potential roles of histones in host defense as antimicrobial agents. Infect Disord Drug Targets 8, 195-205.

Lamond, A. I., and Earnshaw, W. C. (1998). Structure and function in the nucleus. Science 280, 547-553.

Lee, G., Walser, T. C., and Dubinett, S. M. (2009). Chronic inflammation, chronic obstructive pulmonary disease, and lung cancer. Curr Opin Pulm Med.

Maclay, J. D., Rabinovich, R. A., and MacNee, W. (2009). Update in chronic obstructive pulmonary disease 2008. American journal of respiratory and critical care medicine 179, 533-541.

Macnee, W. (2007). Pathogenesis of chronic obstructive pulmonary disease. Clin Chest Med 28, 479-513, v.

Makris, D., Vrekoussis, T., Izoldi, M., Alexandra, K., Katerina, D., Dimitris, T., Michalis, A., Tzortzaki, E., Siafakas, N. M., and Tzanakis, N. (2009). Increased apoptosis of neutrophils in induced sputum of COPD patients. Respir Med 103, 1130-1135.

Mannino, D. M., Davis, K. J., and Kiri, V. A. (2009). Chronic obstructive pulmonary disease and hospitalizations for pneumonia in a US cohort. Respir Med 103, 224-229.

Papayannopoulos, V., and Zychlinsky, A. (2009). NETs: a new strategy for using old weapons. Trends Immunol 30, 513-521.

Pemberton, A. D., Brown, J. K., and Inglis, N. F. (2010). Proteomic identification of interactions between histones and plasma proteins: implications for cytoprotection. Proteomics 10, 1484-1493.

Postma, D. S., and Timens, W. (2006). Remodeling in asthma and chronic obstructive pulmonary disease. Proc Am Thorac Soc 3, 434-439.

Rajendrasozhan, S., Yao, H., and Rahman, I. (2009). Current perspectives on role of chromatin modifications and deacetylases in lung inflammation in COPD. COPD 6, 291-297.

Richens, T. R., Linderman, D. J., Horstmann, S. A., Lambert, C., Xiao, Y. Q., Keith, R. L., Boe, D. M., Morimoto, K., Bowler, R. P., Day, B. J., et al. (2009). Cigarette smoke impairs clearance of apoptotic cells through oxidant-dependent activation of RhoA. American journal of respiratory and critical care medicine 179, 1011-1021.

Salazar, L. M., and Herrera, A. M. (2011). Fibrotic response of tissue remodeling in COPD. Lung 189, 101-109.

Taverna, S. D., Li, H., Ruthenburg, A. J., Allis, C. D., and Patel, D. J. (2007). How chromatin-binding modules interpret histone modifications: lessons from professional pocket pickers. Nat Struct Mol Biol 14, 1025-1040.

Voigt, P., and Reinberg, D. (2011). Histone tails: ideal motifs for probing epigenetics through chemical biology approaches. Chembiochem 12, 236-252.

Weake, V. M., and Workman, J. L. (2010). Inducible gene expression: diverse regulatory mechanisms. Nat Rev Genet 11, 426-437.

Westergren-Thorsson, G., Larsen, K., Nihlberg, K., Andersson-Sjoland, A., Hallgren, O., Marko-Varga, G., and Bjermer, L. (2010). Pathological airway remodelling in inflammation. Clin Respir J 4 Suppl 1, 1-8.

Wiesner, J., and Vilcinskas, A. (2010). Antimicrobial peptides: the ancient arm of the human immune system. Virulence 1, 440-464.

Wood, C., Snijders, A., Williamson, J., Reynolds, C., Baldwin, J., and Dickman, M. (2009). Post-translational modifications of the linker histone variants and their association with cell mechanisms. FEBS J 276, 3685-3697.

Xu, J., Zhang, X., Pelayo, R., Monestier, M., Ammollo, C. T., Semeraro, F., Taylor, F. B., Esmon, N. L., Lupu, F., and Esmon, C. T. (2009). Extracellular histones are major mediators of death in sepsis. Nat Med 15, 1318-1321.

Yokohori, N., Aoshiba, K., and Nagai, A. (2004). Increased levels of cell death and proliferation in alveolar wall cells in patients with pulmonary emphysema. Chest 125, 626-632.

Yu, Y., and Waters, R. (2005). Histone acetylation, chromatin remodelling and nucleotide excision repair: hint from the study on MFA2 in *Saccharomyces cerevisiae*. Cell Cycle 4, 1043-1045.

---

The invention claimed is:

1. A method of treating chronic obstructive pulmonary disease (COPD) in a patient in need of such treatment, the method comprising:
   (a) determining the level of extracellular H3 protein in a test sample of the patient;
   (b) comparing the level of extracellular H3 protein in the test sample with the level of extracellular H3 protein in a control sample;
   (c) determining an elevated level of extracellular H3 protein in the test sample as compared to the level of extracellular H3 protein in the control sample; and
   (d) administering a COPD treatment to the patient having the elevated level of extracellular H3 protein, wherein extracellular H3 protein comprises one or more of H3.1, H3.2, and H3.3.

2. The method of claim 1 wherein the control sample is from a healthy person without COPD.

3. The method of claim 1 wherein the control sample is from an ex-smoker without COPD.

4. The method of claim 1 wherein the control sample is from a GOLD 0 patient.

5. The method of claim 1 wherein the test sample is from the airway of the patient.

6. The method of claim 5 wherein the test sample comprises mucus plugs from the airway of the patient.

7. The method of claim 5 wherein the test sample comprises cell debris that was attached to the cilia of airway epithelial cells of the patient.

8. The method of claim 1 wherein the test sample comprises bronchoalveolar fluid of the patient.

9. The method of claim 1 wherein extracellular H3 protein is measured in a test sample comprising a biological fluid sample of the patient.

10. The method of claim 9 wherein the biological fluid is plasma or serum.

11. A method of treating chronic obstructive pulmonary disease (COPD) in a patient in need of such treatment comprising:
    administering a COPD treatment to a patient in which a test sample from the patient has been determined to contain an elevated level of extracellular H3 protein compared to the level of extracellular H3 in a control sample, wherein extracellular H3 protein comprises one or more of H3.1, H3.2, and H3.3.

12. The method of claim 11 wherein the control sample is from a healthy person without COPD, form an ex-smoker without COPD, or from a Global Initiative for Chronic Obstructive Lung Disease (GOLD) 0 patient.

13. The method of claim 11 wherein the test sample is from the airway of the patient.

14. The method of claim 13 wherein the test sample comprises mucus plugs from the airway of the patient.

15. The method of claim 13 wherein the test sample comprises cell debris that was attached to the cilia of airway epithelial cells of the patient.

16. The method of claim 11 wherein the test sample comprises bronchoalveolar fluid of the patient.

17. The method of claim 11 wherein extracellular H3 protein is measured in a test sample comprising a biological fluid sample of the patient.

18. The method of claim 17 wherein the biological fluid is plasma or serum.

* * * * *